United States Patent
Veeneman et al.

(10) Patent No.: US 6,686,371 B2
(45) Date of Patent: Feb. 3, 2004

(54) NON-STEROIDAL, TETRACYLIC COMPOUNDS FOR ESTROGEN-RELATED TREATMENTS

(75) Inventors: Gerrit Herman Veeneman, Schaijk (NL); Eduard Willem De Zwart, Oss (NL); Hubert Jan Jozef Loozen, Uden (NL); Jordi Mestres, Edinburgh (GB)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/240,129

(22) PCT Filed: Mar. 21, 2001

(86) PCT No.: PCT/EP01/03187

§ 371 (c)(1),
(2), (4) Date: Dec. 2, 2002

(87) PCT Pub. No.: WO01/72713

PCT Pub. Date: Oct. 4, 2001

(65) Prior Publication Data

US 2003/0144313 A1 Jul. 31, 2003

(30) Foreign Application Priority Data

Mar. 27, 2000 (EP) .............................. 00201103
Mar. 27, 2000 (EP) .............................. 00201105

(51) Int. Cl.[7] ..................... A61K 31/473; C07D 221/18
(52) U.S. Cl. .................. 514/284; 546/61; 568/632; 568/633; 568/634; 568/719; 514/721; 514/732
(58) Field of Search .................. 514/284, 721, 514/732; 546/61; 568/632, 633, 634, 719

(56) References Cited

U.S. PATENT DOCUMENTS

| | | |
|---|---|---|
| 5,147,880 A | 9/1992 | Jones |
| 5,688,808 A | 11/1997 | Jones et al. |

FOREIGN PATENT DOCUMENTS

EP  0 785 191 A  7/1997
WO  92 21661 A  12/1992

OTHER PUBLICATIONS

Beisler J A: "Potential Antitumor Agents. 1. Analogs of Comptothecin"; Journal of Medicinal Chemistry, American Chemical Society, vol. 14, No. 11, 1971, pp. 1116–1118; p. 1117, compounds 8 to 13; table I.

Morreal C E et al: "Antiestrogenic Properties of Substituted Benzaanthracene–3, 9–Diols"; Journal of Medicinal Chemistry, American Chemical Society, vol. 25, No. 3, 1982, pp. 323–326; scheme 1, compounds 1, 2, 3; table 1.

Primary Examiner—Charanjit S. Aulakh
(74) Attorney, Agent, or Firm—Mark W. Minstead

(57) ABSTRACT

The invention provides non-steroidal estrogenic compounds with estrogenic and anti-estrogenic compounds effects for treatment of estrogen-deficiency related disorders, which compounds are having formula (I) wherein, one of $R^a$ or $R^b$ is $'R^e$; $R^e$ and $'R^e$ are OH, optionally independently etherified or esterified; X is N or —$C(R^1)$—, wherein $R^1$ is $H_1$ halogen, CN, optionally substituted aryl, (1C–4C)alkyl, (2C–4C)alkenyl, (2C–4C)alkynyl or (3C–6C)cycloalkyl, which alkyl, alkenyl, alkynyl and cycloalkyl groups can optionally be substituted with one or more halogens; Y is N or —$C(R^2)$—, with the proviso that X and Y are not both N, wherein $R^2$ has the same meaning as defined for $R^1$; Z is $C(R^3,'R^3)$— or —$C(R^4,\propto R^4)$—$C(R^5,'R^5)$—, wherein $R^3$, $'R^3$, $R^4$, $'R^4$, $R^5$, and $'R^5$, independently arc H, (1C–4C) alkyl, (2C–4C)alkenyl or (3C–6C) cycloalkyl, which alkyl, alkenyl and cycloalkyl groups can optionally be substituted with one or more halogens. These compounds are useful for estrogen-receptor related treatments in view of a desirable profile of activity for estrogen α and estrogen β receptors.

(I)

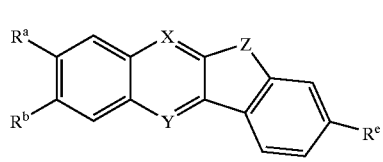

20 Claims, No Drawings

NON-STEROIDAL, TETRACYLIC COMPOUNDS FOR ESTROGEN-RELATED TREATMENTS

FIELD OF THE INVENTION

The invention is in the field of non-steroidal compounds for estrogen-related treatments. Estrogenic and anti-estrogenic compounds have a generally recognised utility for estrogen-receptor related medical treatments, such as those for contraception and for treatment of menopausal complaints, osteoporosis, and estrogen dependent tumour control.

BACKGROUND OF THE INVENTION

More precisely, the invention pertains to non-steroidal estrogen receptor modulating compounds with an 11H-benzo[b]fluorene, an 11H-indeno-[1,2-b]quinoline, a benz[a]anthracene or analogous skeleton. Analogous compounds with claimed usefulness in estrogen related medical treatments are described in U.S. Pat. No. 5,688,808 (1H-indeno[1,2-g]quinolines) and Morreal et al., J.Med.Chem., 1982, Vol 25, pp 323–326 (benz[a]anthracenes). Related estrogen receptor modulating compounds are described in EP 524, 742, EP 832 881 and U.S. Pat. No. 5,147,880 (1H-benzo[a]fluorenes].

Whereas further improvements for treatment of estrogen-related diseases remains desirable and there is a keen interest in compounds with affinity for the estrogen receptor, new compounds with an 11H-benzo[b]fluorene, an 11H-indeno-[1,2-b]quinoline, a benz[a]anthracene or analogous skeleton and affinity for the estrogen receptor cannot be learnt from these documents. The interest in new compounds with affinity for the estrogen receptor stems from unsatisfactory results with known estrogenic compounds for osteoporose treatment and treatment of other postmenopausal complaints and from the discovery of two distinct types of receptors, denoted ERα and ERβ (see Mosselman et al., *FEBS Letters* 392 (1996) 49–53 as well as EP-A-0 798 378). Since these receptors have a different distribution in human tissue, the finding of compounds which possess a selective affinity for either of the two is an important technical progress, making it possible to provide an improved and/or more selective treatment in the field of estrogen-receptor related medical treatments, such as those for contraception and for treatment of menopausal complaints, osteoporosis, and estrogen dependent tumour control, with a lower burden of estrogen-related side-effects.

DETAILED DESCRIPTION OF THE INVENTION

This invention provides new tetracyclic non-steroidal compounds having the formula I

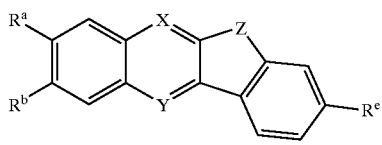

Formula I wherein,
one of $R^a$ or $R^b$ is $'R^e$;
$R^e$ and $'R^e$ are OH, optionally independently etherified or esterified;

X is N or —($R^1$)—, wherein $R^1$ is H, halogen, CN, optionally substituted aryl, (1C–4C)alkyl, (2C–4C)alkenyl, (2C–4C)alkynyl or (3C–6C)cycloalkyl, which alkyl, alkenyl, alkynyl and cycloalkyl groups can optionally be substituted with one or more halogens;

Y is N or —C($R^2$)—, with the proviso that X and Y are not both N, wherein $R^2$ has the same meaning as defined for $R^1$;

Z is —C($R^3$,$'R^3$)— or —C($R^4$,$'R^4$)—C($R^5$,$'R^5$)—, wherein $R^3$, $'R^3$, $R^4$, $'R^4$, $R^5$, and $'R^5$, independently are H, (1C–4C)alkyl, (2C–4C)alkenyl or (3C–6C)cycloalkyl, which alkyl, alkenyl and cycloalkyl groups can optionally be substituted with one or more halogens.

The compounds of this invention have surprising and often selective interactions with estrogen receptors.

The reference to the meanings of $R^1$ in the definition of $R^2$ does not imply that $R^1$ is the same as $R^2$ in a compound as defined above. In fact, a more specific embodiment of this invention is a compound wherein at least one of $R^1$ or $R^2$ is halogen or fluorine substituted methyl.

Depending on the selection of a meaning of $R^3$, $'R^3$, $R^4$, $'R^4$, $R^5$ and $'R^5$, compounds of the invention can have asymmetrically substituted atoms and can exist in enantiomeric pure forms or mixtures of enantimers differing from the usual 50/50 proportion.

Another specific embodiment of the invention is a compound according to formula I wherein X is —C($R^1$)13 and Y is N, having the formula II:

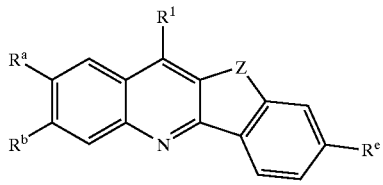

Formula II wherein,
one of $R^a$ or $R^b$ is $'R^e$;
$R^e$ and $'R^e$ are OH, optionally independently etherified or esterified;
Z is —C($R^3$,$'R^3$)— or —C($R^4$,$'R^4$)—C($R^5$,$'R^5$)—, wherein $R^3$, $'R^3$, $R^4$, $'R^4$, $R^5$, and $'R^5$, independently are H, (1C–4C)alkyl, (2C–4C)alkenyl or (3C–6C)cycloalkyl, which alkyl, alkenyl and cycloalkyl groups can optionally be substituted with one or more halogens.

A preferred variant of this embodiment is $R^a$ is $'R^e$ and consequently $R^b$ is H and further meanings are as defined for Formula II above. More preferred is $R^1$ is halogen or fluorine substituted methyl.

Compounds according to formula II in which Z is —C($R^3$,$'R^3$)—, $R^a$ is $'R^e$ and $R^b$ is H have the formula III

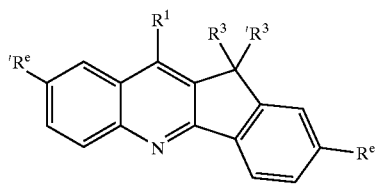

Formula III whereby the symbols have the meaning as defined for Formula II. Such compounds are named 11H-indeno[1,2-b]quinolines according to the convention of the chemical abstracts.

An embodiment of the invention is a compound according to Formula II, in which Z is —C(R$^4$,'R$^4$)—C(R$^5$,'R$^5$)—; R$^a$ is 'R$^e$; R$^b$, R$^4$, 'R$^4$, R$^5$ and 'R$^5$ are H, having the formula IV

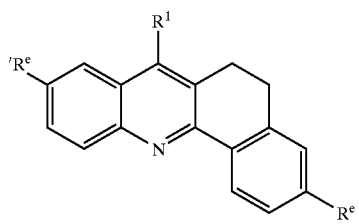

Formula IV wherein,

R$^1$ is H, halogen, CN, optionally substituted aryl, (1C–4C)allyl, (2C–4C)alkenyl, (2C–4C)alkynyl or (3C–6C)cycloalkyl, which alkyl, alkenyl, alkynyl and cycloalkyl groups can optionally be substituted with one or more halogens. Such compounds are named 3,9-dihydroxy-5,6-dihydro-benz[c]acridines. In this embodiment of the invention it is preferred that R$^1$ is halogen or fluorine substituted methyl.

Another embodiment of the invention is a compound having Formula I, wherein X is N, Y is —C(R$^2$)—, R$^a$ is H and R$^b$ is 'R$^e$, having Formula V

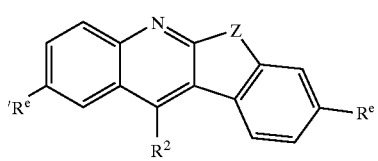

Formula V wherein,

Re and 'R$^e$ are OH, optionally independently etherified or esterified;

Z is —C(R$^3$,'R$^3$)— or —C(R$^4$,'R$^4$)—C(R$^5$,'R$^5$)—, wherein R$^3$, 'R$^3$, R$^4$, 'R$^4$, R$^5$, and 'R$^5$, independently are H, (1C–4C)alkyl, (2C–4C)alkenyl or (3C–6C) cycloalkyl, which alkyl, alkenyl and cycloalkyl groups can optionally be substituted with one or more halogens;

R$^2$ is H, halogen, CN, optionally substituted aryl, (1C–4C)alkyl, (2C–4C)alkenyl, (2C–4C)alkynyl, (3C–6C)cycloalkyl, which alkyl, alkenyl, alkynyl and cycloalkyl groups can optionally be substituted with one or more halogens.

In this embodiment it is preferred that R$^2$ is halogen or fluorine substituted methyl and R$^3$, 'R$^3$, R$^4$, 'R$^4$, R$^5$, and 'R$^5$, independently are H or methyl. More preferred is that Z is —C(R$^4$,'R$^4$)—C(R$^5$,'R$^5$)—, wherein R$^4$, 'R$^4$, R$^5$, and 'R$^5$, are H.

Another embodiment of this invention is a compound according to formula I, wherein X is —C(R$^1$)—, Y is —C(R$^2$)—, having Formula VI

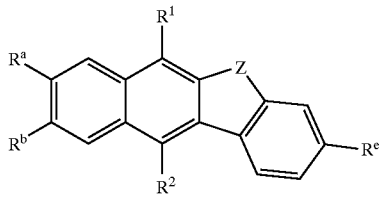

Formula VI wherein, one of R$^a$ or R$^b$ is 'R$^e$;

R$^e$ and 'R$^e$ are OH, optionally independently etherified or esterified;

R$^1$ and R$^2$ independently are H, halogen, CN, optionally substituted aryl, (1C–4C)alkyl, (2C–4C)alkenyl, (2C–4C)alkynyl or (3C–6C)cycloalkyl, which alkyl, alkenyl, alkynyl and cycloalkyl groups can optionally be substituted with one or more halogens;

Z is —C(R$^3$,—R$^3$)— or —C(R$^4$,'R$^4$)—C(R$^5$,'R$^5$)—, wherein R$^3$, 'R$^3$, R$^4$, 'R$^4$, R$^5$, and 'R$^5$, independently are H, (1C–4C)alkyl, (2C–4C)alkenyl or (3C–6C) cycloalkyl, which alkyl, alkenyl and cycloalkyl groups can optionally be substituted with one or more halogens. In this embodiment it is preferred that R$^1$ or R$^2$ is halogen or fluorine substituted methyl.

Also preferred in this embodiment are those compounds according to Formula VI whereby R$^a$ is 'R$^e$; R$^b$ is H; Z is —C(R$^4$,'R$^4$)—C(R$^5$,'R$^5$)—, wherein R$^4$, 'R$^4$, R$^5$, and 'R$^5$ are H, which compounds are having Formula VII

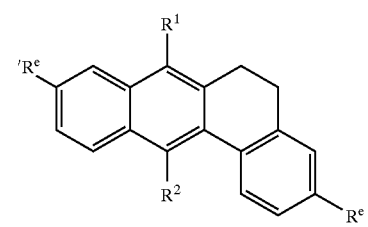

Formula VII wherein,

R$^e$ and 'R$^e$ are OH, optionally independently etherified or esterified;

R$^1$ and R$^2$ independently are H, halogen, CN, optionally substituted aryl, (1C–4C)alkyl, (2C–4C)alkenyl, (2C–4C)alkynyl or (3C–6C)cycloalkyl, which alkyl, alkenyl, alkynyl and cycloalkyl groups can optionally be substituted with one or more halogens, whereby it is preferred that R$^1$ is halogen or methyl, optionally fluorine substituted, and R$^2$ is hydrogen, which compounds are named 5,6-dihydro-3,9-dihydroxy-benz[a] anthracenes;

or compounds according to formula VI, whereby Z is —C(R$^3$,'R$^3$)—, having Formula VIII

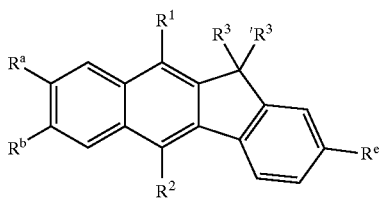

Formula VIII wherein, one of $R^a$ or $R^b$ is '$R^e$;

$R^1$ and $R^2$ independently are H, halogen, CN, optionally substituted aryl, (1C–4C)alkyl, (2C–4C)alkenyl, (2C4C)alkynyl or (3C–6C)cycloalkyl, which alkyl, alkenyl, alkynyl and cycloalkyl groups can optionally be substituted with one or more halogens, whereby it is preferred that $R^1$ is halogen or methyl, optionally substituted with fluorine, and $R^2$ is hydrogen;

$R^3$ and '$R^3$ independently are H or $CH^3$, which compounds are named 11H-2-hydroxy-benzo[b]fluorenes.

In view of high selectivity for the ERβ, more preferred compounds are compounds according to formula VIII, wherein $R^a$ is '$R^e$, $R^b$ is H, $R^3$, '$R^3$ are H or methyl, $R^1$ or $R^2$ is H and the other of $R^1$ or $R^2$ is halogen, CN, optionally substituted aryl, (1C–4C)alkyl, (2C–4C)alkenyl, (2C–4C)alkynyl or (3C–6C)cycloalkyl, which alkyl, alkenyl, alkynyl and cycloalkyl groups can optionally be substituted with one or more halogens, whereby it is preferred to select for $R^1$ or $R^2$ halogen or methyl, optionally substituted with fluorine. In general it is preferred that $R^3$ and '$R^3$ are H.

The best mode of the invention, in view of selectivity for the ERβ, is a compound according to Formula IX

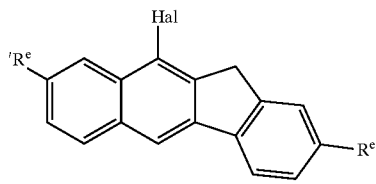

Formula IX wherein, $R^e$ and '$R^e$ are OH, optionally independently etherified or esterified;

Hal is fluorine, chlorine, bromine or fluorinated methyl, whereby from these possibilities for Hal the chlorine is most preferred.

The ester and ether compounds in the collection of compounds according to the invention often have activity as prodrug. Preferred ester and ether prodrugs are carboxylic acid esters or alkyl ethers on one or both hydroxyl groups, and more preferred prodrugs are (2C–6C)carboxylic acid esters, such as esters of (iso)butanoic acid, or (1C–4C) alkyl ethers. A prodrug is defined as being a compound which converts in the body of a recipient to a compound as defined by the formulas I to IX. Notably, the hydroxy groups as depicted in the formulas above can for example be substituted by alkyl*oxy, alkenyl*oxy, acyl*oxy, aroyloxy, alk*oxycarbonyloxy, sulfonyl groups or phosphate groups, whereby the carbon chain length of the groups denoted with an asterisk (*) is not considered to be sharply delimited, while aroyl generally will comprise a phenyl, pyridinyl or pyrimidyl, which groups can have substitutions customary in the art, such as alkyl*oxy, hydroxy, halogen, nitro, cyano, and (mono-, or dialkyl*-)amino. The length of the alkyl, alkenyl and acyl groups is selected depending on the desired properties of the prodrugs, whereby the longer chained prodrugs with for example lauryl or caproyl chains are more suitable for sustained release and depot preparations. It is known that such substituents spontaneously hydrolyse or are enzymatically hydrolysed to the free hydroxyl substituents on the skeleton of the compound. Such prodrugs will have biological activity comparable to the compounds to which they are converted in the body of the recipients. The active compound to which a prodrug is converted is called the parent compound. The onset of action and duration of action as well as the distribution in the body of a prodrug may differ from such properties of the parent compound.

Substitution variants of the compounds of the present invention are possible for similar use. A substitution variant is defined to be a compound which comprises in its molecular structure the structure as defined by the formula I. The skilled person inspecting the group of compounds provided by the present invention will immediately understand that modification by a substituent to the skeleton can yield a compound with similar biological activity as the compound without this particular substituent. It is common practise in the art to test such substitution variants for the expected biological activity so that it is a routine skill to obtain useful substitution variants of compounds according to the invention.

Other terms used in this description have the following meaning:

alkyl is a branched or unbranched alkyl group, for example methyl, ethyl, propyl, isopropyl, butyl, sec-butyl, tert-butyl, hexyl, octyl, capryl, or lauryl;

alkenyl is a branched or unbranched alkenyl group, such as ethenyl, 2-butenyl, etc.;

alkynyl is a branched or unbranched alkynyl group, such as ethynyl and propynyl.

halogen refers to fluorine, chlorine, bromine and iodine;

aryl is a mono- or polycyclic, homo- or heterocyclic aromatic ring system, such as phenyl, naphtyl or pyridinyl; a monocyclic ring with 6 atoms is preferred for use;

aroyl is arylcarbonyl such as a benzoyl group;

alkanoyl means an oxo-substituted alkyl group, such as 2-oxobutyl or an acyl group;

acyl is an alkylcarbonyl group.

The prefixes (1C–4C), (2C–4C) etc. have the usual meaning to restrict the meaning of the indicated group to those with 1 to 4, 2 to 4 etc. carbon atoms.

The estrogen-receptor affinity profile of the compounds according to the present invention, makes them suitable as improved estrogens or anti-estrogens, in the sense that they can be used for estrogen-receptor related medical treatments, such as those for contraception or for treatment or prevention of benign prostate hypertrophy, cardiovascular disorders, menopausal complaints, osteoporosis, estrogen dependent tumour control or central nervous system disorders such as depression or Alzheimer's disease.

In particular those compounds which have selective affinity for the ERα receptor are suitable for estrogen-receptor related medical treatments under diminished estrogen-related side-effects. This is most desirable when these compounds are used in the treatment of osteoporosis, cardiovascular disorders and central nervous system disorders such as depression or Alzheimer's disease.

The compounds of the invention can be produced by various methods known in the art of organic chemistry in general. More specifically the routes of synthesis as illustrated in the schemes and examples can be used. A general description of the synthesis of halogenated benzo[b]fluorenes is depicted in scheme 1.

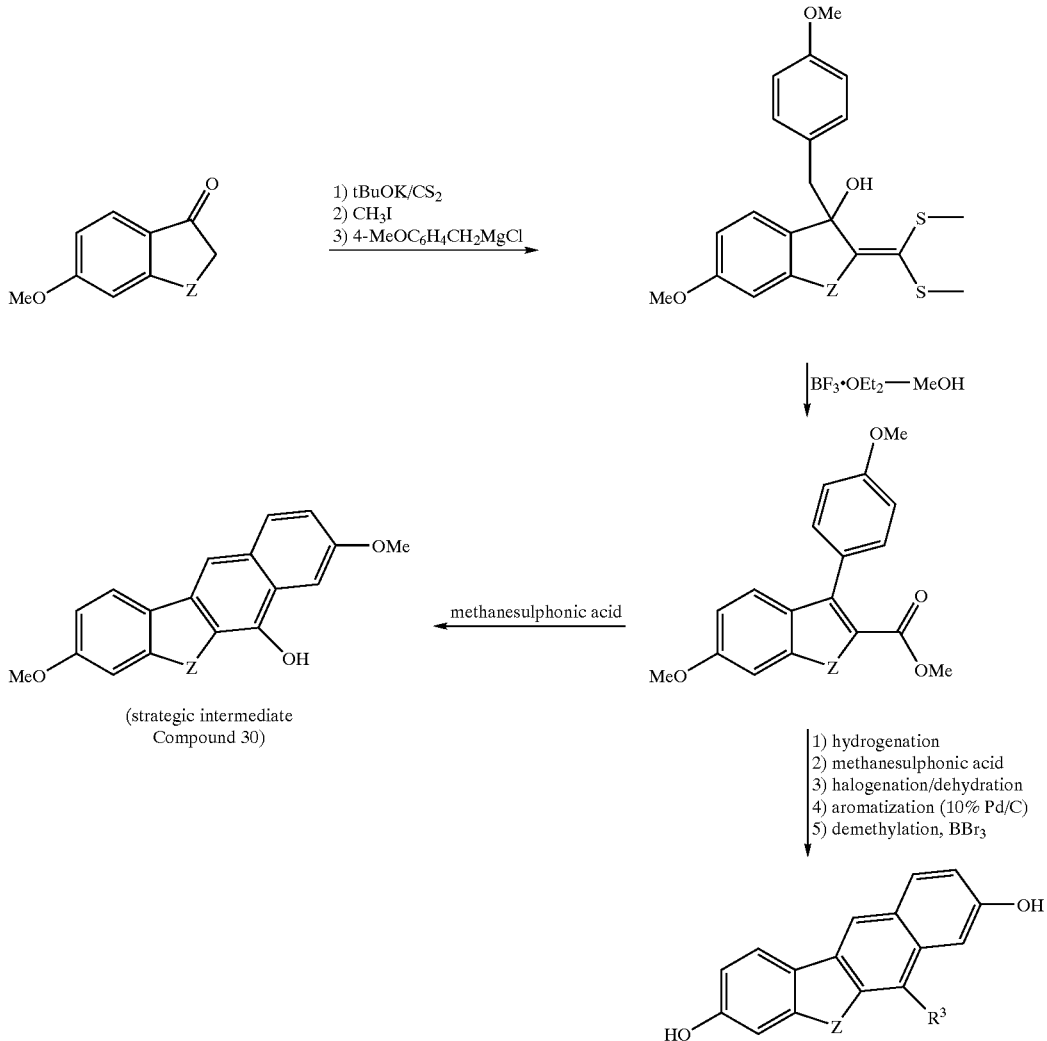

Scheme 1.

General procedure to prepare benzofluorenes
Abbreviations used in the scheme are: tBu is tertiairy butyl, Me is methyl and Et is ethyl; $R^3$ is a halogen originating from the halogenation step; Z can have any meaning as defined for Formula I.

The intermediate for further substitutions (strategic intermediate; e.g. compound 30 in examples 9, 10 and 11) can be made from its precursor in scheme 1 by adding methanesulphonic acid to the precursor and warming (about 60° C.) for some time (about 30 minutes).

Ester prodrugs can be made by esterification of compounds with free hydroxyl groups by reaction with appropriate acyl chlorides in pyridine.

The present invention also relates to a pharmaceutical composition comprising the non-steroidal compound according to the invention mixed with a pharmaceutically acceptable auxiliary, such as described in the standard reference Gennaro et al., *Remmington's Pharmaceutical Sciences*, (18th ed., Mack publishing Company, 1990, see especially Part 8: Pharmaceutical Preparations and Their Manufacture.). The mixture of the compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants. polymeric binders and the like is contemplated. In general any pharmaceutically acceptable additive which does not interfere with the function of the active compounds can be used. The compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of the non-steroidal compound according to the invention for the manufacture of a medicament for estrogen-receptor related treatments and treatment of estrogen-receptor related disorders such as peri- and/or post-menopausal complaints. Thus the invention also pertains to the medical indications of peri- and/or post-menopausal (climacteric) complaints and osteoporosis, i.e. a method of treatment in the field of hormone replacement therapy (HRT), comprising the administration to a patient, being a woman, of a compound as described hereinbefore (in a suitable pharmaceutical dosage form).

Further, the invention relates to the use of the non-steroidal compound according to the invention in the manufacture of a medicament having contraceptive activity. Thus the invention also pertains to the medical indication of contraception, i.e. a method of contraception comprising the administration to a subject, being a woman or a female animal, of a progestogen and an estrogen as is customary in the field, wherein the estrogen is a compound as described hereinbefore (in a suitable pharmaceutical dosage form).

Finally the invention relates to the use of the non-steroidal compound for the manufacture of a medicament having selective estrogenic activity, such a medicament being generally suitable in the area of HRT (hormone replacement therapy).

The dosage amounts of the present compounds will be of the normal order for estrogenic compounds, e.g. of the order of 0.01 to 100 mg per administration.

The invention is further illustrated hereinafter with reference to some unlimitative examples and the corresponding formula schemes referred to.

EXAMPLES

In the examples the compounds are identified with numbers, for example 1a, 1b, 2 etc.. These numbers refer to the definitions of the compounds in the schemes.

Example 1

Scheme 2.

Synthesis of specified indenoquinolines:

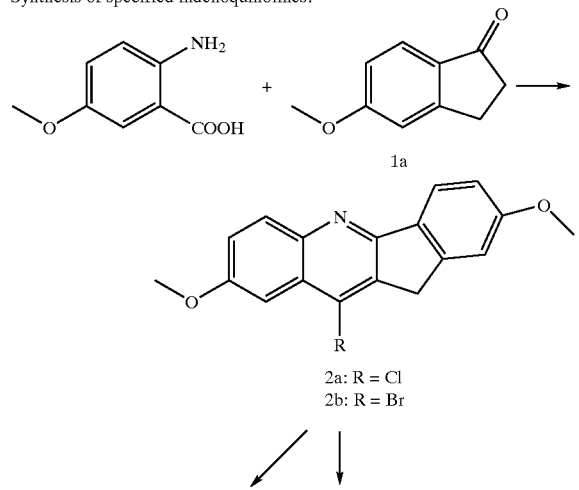

-continued

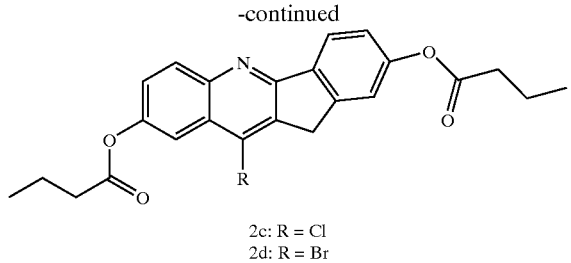

2c: R = Cl
2d: R = Br

Example 1a 10-chloro-2,8-dimethoxy-11H-indeno[1,2-b]quinoline: 2a

Guided by the procedure of Yamato et al [J. Med. Chem. 32 (1989) 1295 –1300] a mixture of 5-methoxy-anthranilic acid (2.0 mmol) and 5-methoxy-indan-1-one 1a (2.4 mmol) was heated for 1 hour at 170° and 2 hours at 200° C. The resulting precipitate was collected and washed successively with pyridine and ether.

The solid material was taken up in $POCl_3$ (6 ml) and refluxed for 2 hours. The reaction was poured into ice water and neutralized with ammonia. The solid material was filtered off, washed with water and dried in vacuo. 80 μmol of the solid and 0.5 g pyridine hydrochloride were heated at 200° C. for 1–1.5 hours, The reaction mixture was cooled to room temperature and taken up in $NaHCO_3$(aq) and extracted with ethyl acetate.

Purification by chromatography on silica gel (dichloromethane/methanol or toluene/acetone) afforded pure 2a in 37% yield.(Rf=0.47 toluene/acetone (3:2)); ESI-MS: M+H=284, M−H=282.

Example 1b 10-bromo-2,8-dimethoxy-11H-indeno[1,2-b]quinoline: 2b Compound 2b was prepared in 11% yield, in the same fashion as described for the preparation of 2a, but using $POBr_3$ (2.5 g) instead of $POCl_3$ (Rf=0.47 toluene/acetone (3:2)); ESI-MS: M+H=328+330 (1:1).

Example 1c

Dibutyryl Ester of 10-chloro-2,8-dihydroxy-1H-indeno[1,2-b]quinoline: 2c Compound 2a (13 μmol) was treated with n-butyryl chloride (10 μl) in pyridine (1 ml) for 2 hours. The mixture was poured into water, extracted with ethyl acetate and concentrated. $SiO_2$-chromatography of the residue gave pure 2c in 45% yield. (Rf=0.67 heptane/ethyl acetate (3:2)); ESI-MS: M+H 424.2.

Example 1d

Dibutyryl Ester of 10-bromo-2,8-dihydroxy-11H-indeno[1,2-b]quinoline: 2d Compound 2b (42 μmol) was treated with n-butyryl chloride (30 μl) in pyridine (2 ml) for 15 hours. The mixture was poured into water, extracted with ethyl acetate and concentrated. $SiO_2$-chromatography of the residue gave pure 2d in 49% yield. (Rf=0.63 heptane/ethyl acetate (3:2)); ESI-MS: M+H=468.0+470.0 (1:1).

Example 2

10-methyl-2,8-dihydroxy-11H-indeno[1,2-b]quinoline: 4

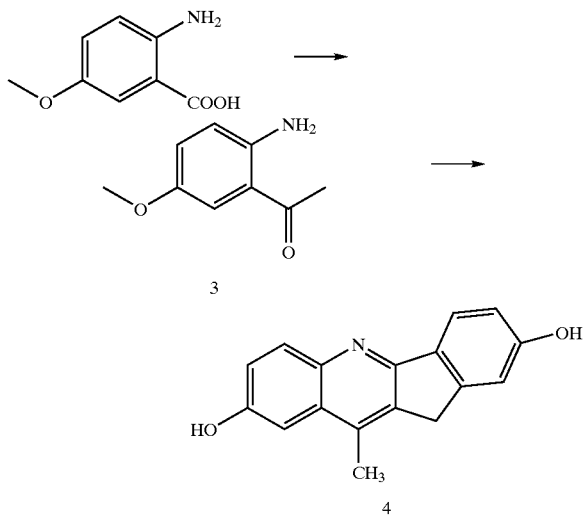

Compound 4 was synthesized following the procedure described by Czarny et al [*Heterocycles*, (1997) 2089–2092]. Anthranilic acid (2.0 mmol) in THF (10 ml) was treated with methyllithium 1.6M in ether (6.0 mmol) at −20° C. and was allowed to warm to room temperature over 2 hours. The mixture was poured into NH$_4$Cl (aq), extracted with ethyl acetate and dried. Purification of the residue by SiO$_2$-chromatography (heptane/ethyl acetate) gave pure 2-amino-5-methoxy-acetophenone 3 in 44% yield. Compound 3 (0.6 mmol) was condensed with 5 methoxy indanone (0.8 mmol) in acetic acid (3 ml) and 3 drops of sulfuric acid at 115° C. for 3 hours. After cooling to room temperature the precipitate was filtered off, washed with acetic acid and dried in vacuo. The solid material was taken up in 1.5 ml CH$_2$Cl$_2$ and BBr$_3$ (0.23 mmol) was added. After 2 hours the mixture was carefully poured into saturated NaHCO$_3$(aq) and extracted with ethyl acetate. The organic layer was dried over MgSO$_4$ and concentrated. Purification on silica (toluene/ethyl acetate) afforded pure 4 in 54% yield. (Rf=0.29 toluene/acetone (3:2)); ESI-MS: M+H= 264.0.

Example 3

10-phenyl-2,8-dihydroxy-11H-indeno[1,2-b]quinoline: 5

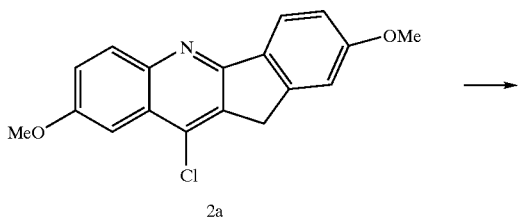

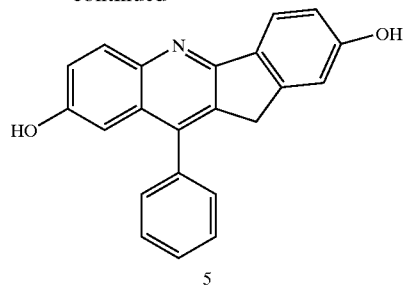

2,8-dimethoxy-10-phenyl indeno-quinoline 5 was prepared following the procedure of Ali et at (*Tetrahedron*, 48 (1992) 8117–81261. 2e (160 μmol), phenylboric acid (25 mg), Na$_2$CO$_3$(aq) (180 μl 2M), Pd(PPh$_3$)$_4$ (6 mg) and ethanol (55 μl) in toluene (2 ml) were refluxed for 48 hours. The reaction mixture was poured into water, extracted (CH$_2$Cl$_2$) and dried. The residue was taken up in ethylene diamine (1 ml) and CH$_2$Cl$_2$ (0.5 ml) and stirred at 80°C. for 1 hour. The mixture was acidified (2N HCl), extracted (CH$_2$Cl$_2$) and dried. SiO$_2$-chromatography (heptane/ethyl acetate) of the residue gave pure 10-phenyl indeno-quinoline. Demethylation with pyridine hydrochloride at 200° C., followed by chromatography on silica gel (dichloromethane/methanol) afforded pure 5 in 44% yield.(Rf=0.29 dichloromethane/methanol (9:1)):ESI-MS: M+H=326.2, M−H=324.0.

Example 4

General procedure A: condensation of 5-methoxy-anthranilic acid with a keton, such as compound 1a, 1b, 1e, 1d or 1e in schemes 5–8, and subsequent chlorination.

Guided by the procedure of Yamato et at [*J. Med. Chem.* 32 (1989) 1295–1300] a mixture of 5-methoxy-anthranilic acid (2.0 mmol) and a keton 1a–1e (2.4 mmol) was heated for 1 hour at 170° and 2 hours at 200° C. The resulting precipitate was collected and washed successively with pyridine and ether.

The solid material was taken up in POCl$_3$ (6 ml) and refluxed for 2 hours. The reaction was poured into ice water and neutralized with ammonia. The solid material was filtered off, washed with water and dried in vacuo.

General procedure B: demethylation with pyridine hydrochloride. 70 μmol of the compound to be demethylated and 500 mg pyridinium chloride were heated at 200° C. for 1.5 hours, after which the cooled mixture was taken up in NaHCO$_3$(aq) and extracted with ethyl acetate. The organic layer was dried over MgSO$_4$ and concentrated. The residue was purified by SiO$_2$-chromatography (dichloromethane/methanol or toluene/acetone).

General procedure C: demethylation with HBr. 70 μmol of the compound to be demethylated and 3 ml HBr (48% in water) were refluxed overnight, after which the cooled mixture was taken up in NaHCO$_3$(aq) and extracted with ethyl acetate. The organic layer was dried over MgSO$_4$ and concentrated. The residue was purified by SiO$_2$-chromatography (toluene/acetone).

General procedure D: demethylation with BBr$_3$. BBr$_3$ (0.53 mmol) was added to a solution of 0.18 mmol of the compound to be demethylated in 2 ml dry CH$_2$C$_{12}$ and the resulting mixture was stirred at roomtemperature for 1 hour. The mixture was carefully poured into sat. NaHCO$_3$ (aq) and extracted with ethyl acetate. The organic layer was dried over MgSO$_4$ and concentrated. Purification by SiO$_2$-chromatography (toluene/ethyl acetate or toluene/acetone).

Scheme 5

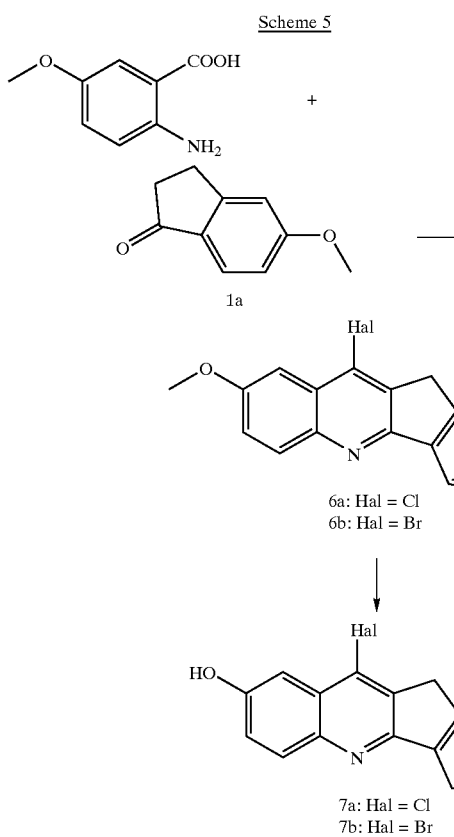

6a: Hal = Cl
6b: Hal = Br

7a: Hal = Cl
7b: Hal = Br

Example 4a 10-chloro-2,8-dihydroxy-11H-indeno[1,2-b]quinoline: 7a 5-methoxy-anthranilic acid and 5-methoxy-indan-1-one were condensed using general procedure A to give 6a in 44% (Rf=0.57 heptane/ethyl acetate (3:2)); ESI-MS: M+H= 312.0. 6a was demethylated using to procedure C to give 7a in 84% yield. (Rf=0.47 toluene/acetone (3:2)); ESI-MS: M+H=284, M−H=282.

Example 4b 10-bromo-2,8-dihydroxy-11H-indeno[1,2-b]quinoline: 7b 5-methoxy-anthranilic acid and 5-methoxy-indan-1-one 1a were condensed following general procedure A using POBr$_3$ instead of POCl$_3$ to give 6b in 67% (Rf=0.55 heptane/ethyl acetate (3:2)); ESI-MS: M+H=355+357 (1:1). 6b was demethylated using general procedure B to give 7b in 16% (Rf=0.47 toluene/acetone (3:2)); ESI-MS: M+H= 328+330 (1:1).

Scheme 6

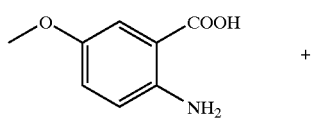

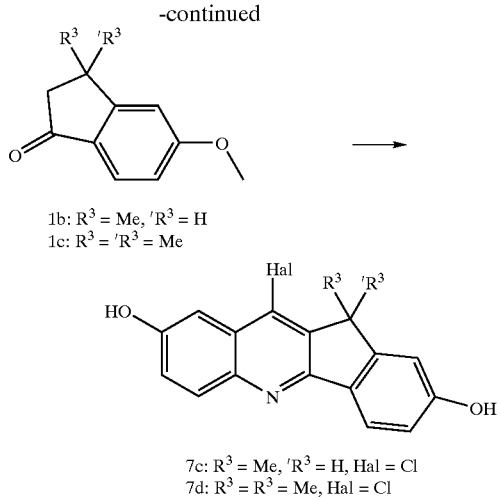

1b: R$^3$ = Me, ′R$^3$ = H
1c: R$^3$ = ′R$^3$ = Me

7c: R$^3$ = Me, ′R$^3$ = H, Hal = Cl
7d: R$^3$ = ′R$^3$ = Me, Hal = Cl

Example 4c 10-chloro-1-methyl-2,8-dihydroxy-11H-indeno[1,2-b]quinoline: 7c Compound 7c was prepared by condensing 5-methoxy-anthranilic acid and 5-methoxy-3-methyl-indan-1-one 1b using general procedure A, followed by demethylation using general procedure B to give 7c in 27% (Rf=0.19 toluene/acetone (3:2)); ESI-MS: M+H=298.0, M−H=296.0.

Example 4d 10-chloro-1,1-dimethyl-2,8-dihydroxy-11H-indeno[1,2-b]quinoline: 7d Compound 7d was prepared by condensing 5-methoxy-anthranilic acid and 5-methoxy-3,3-dimethyl-indan-1-one 1c using general procedure A, followed by demethylation using general procedure B to give 7d in 2% (Rf=0.30 toluene/acetone (3:2)); ESI-MS: M+H=312.0, M−H=310.0.

Example 4e 12-chloro-4,10-dihydroxy-5,6-dihydro-benz[a]acridine 8

Scheme 7

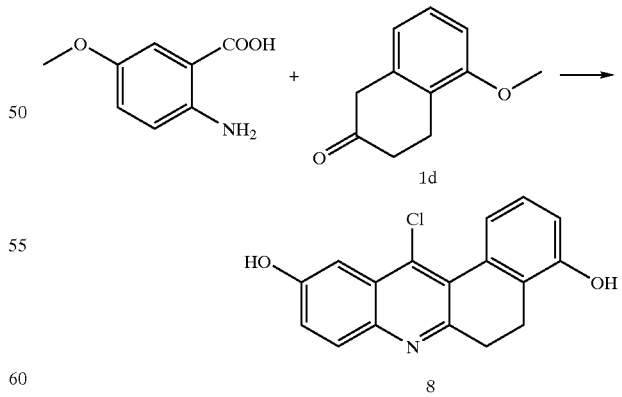

Compound 8 was prepared by condensing 5-methoxy-anthranilic acid and 5-methoxy-3,4-dihydro-1H-naphtalen-2-one 1d using general procedure A followed by demethylation using general procedure D to give 8 in 15% (Rf=0.46 toluene/acetone (3:2)); ESI-MS: M+H=298.0, M−H=295.8.

Example 4f
7-chloro-3,9-dihydroxy-5,6-dihydro-benz[c]acridine: 10
Scheme 8
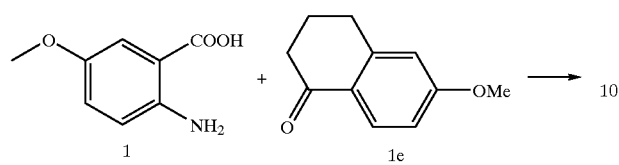
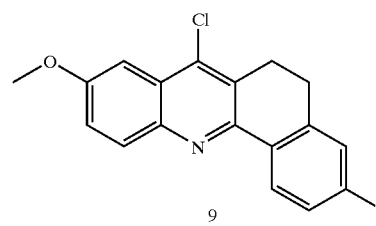
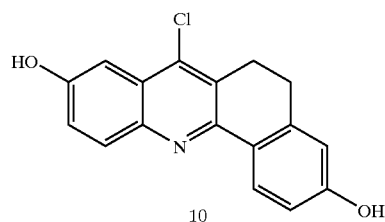
5-methoxy-anthranilic acid and 6-methoxy-3,4-dihydro-2H-naphtalen-1-one 1e were condensed using general procedure A to give 9 in 61% (Rf=0.67 heptane/ethyl acetate (3:2)); ESI-MS: M+H=326.0. 9 was demethylated using general procedure C to give 10 in 73% yield. (Rf=0.55 toluene/acetone (3:2)); ESI-MS: M+H=298,0, M−H=296.2.
Example 5
Scheme 9
Tf in the scheme means triflate
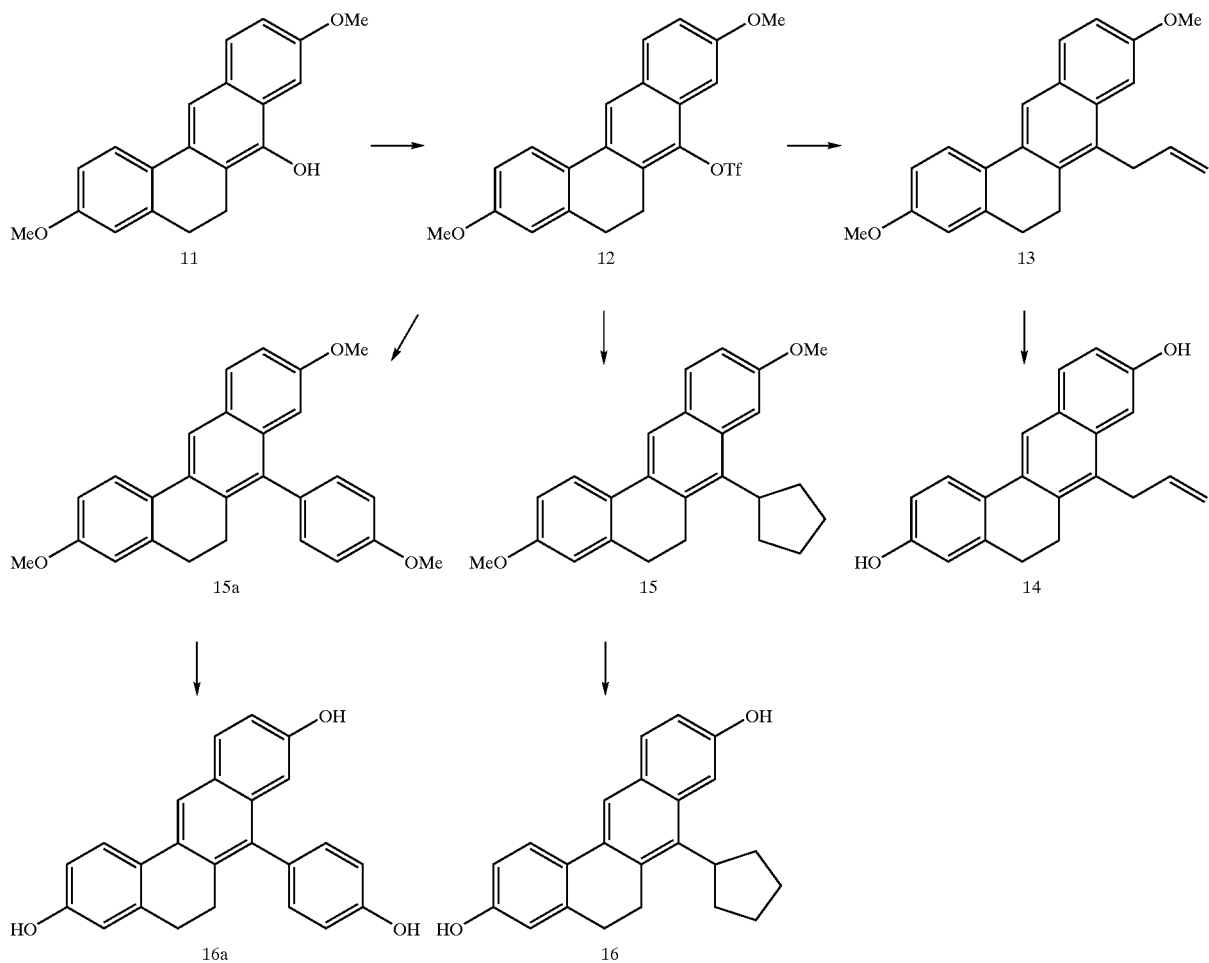

To 1 g of phenol 11 in in 15 ml of dry pyridine was added at 0° C., 0.66 ml of triflic anhydride. The mixture was stirred for 1 hr. Then ice water was added and the product extracted with ethyl acetate. The crude material was purified by chromatography (hept./ethyl acetate), to provide 1.38 g of 12; $R_f$ 0.60 (hept./ethyl acetate 7/3), NMR (CDCl$_3$) δ2.87 and 3.10 (2× m, CH$_2$CH$_2$), 3.87 and 3.95 (2× s, OCH$_3$), 8.03, 7.77, 7.30, 7.15, 6.89, 6.81 (7 aromatic protons).

A mixture consisting of 153 mg of LiCl, 32 mg of PdCl$_2$(PPh$_3$)$_2$, and 200 mg of 12 in 5 ml of DMF was stirred for 30 min at RT. Then 0.18 ml of allyltributyltin was added by syringe and the reaction was heated at reflux for 1 hr. After cooling to RT, water was added and the product was extracted with ethyl acetate. Chromatographic purification (hept/ethyl acetate) provided 190 mg of 3,9-dimethoxy-7-prop-2-enyl-5,6-dihydro-benz[a]anthracene, 13; $R_f$ 0.61 (hept/ethyl acetate 7/3), NMR (CDCl$_3$) δ2.86 and 3.02 (2× m, CH$_2$CH$_2$), 3.03 and 3.86 (2× s, OCH$_3$), 4.95–5.07 (4 m, allylic-CH$_2$), 6.02–6.13 (m, 1, allylic CH).

Deprotection of the methyl ethers was effected with sodium ethanethiolate. This was prepared from 0.46 g of 50% sodiumhydride dispersion (mineral oil) and 1.1 ml of ethanethiol in 8 ml of DMF at 0° C. After stirring this for ½ hr, a solution of 190 mg of 13 in 2 ml of DMF was added and the mixture was refluxed for 3 hr. The reaction was cooled diluted with water, acidified and extracted with ethyl acetate. Purification of the product thus isolated was effected by preparative HPLC to remove some cis and trans propenyl isomers, formed during the reaction. Thus 22 mg of crystalline 3,9-dihydroxy-7-prop-2-enyl-5,6-dihydro-benz[a]anthracene,14, was isolated, Mp 221–222° C.; $R_f$ 0.22 (hept/ethyl acetate 7/3). NMR (DMSO) δ2.70 and 2.89 (2× m, CH$_2$CH$_2$), 4.90–5.04 (4 m, allylic-CH$_2$), 5.98–6.08 (m, 1, allylic CH).

To a mixture of 250 mg of triflate 12 and 30 mg of NiCl2.DPPE in 11 ml of toluene was added 0.43 ml of a 2M-ether solution of cyclopentylmagnesium bromide. The reaction was heated during 1 hr at 60° C. and then poured into sat.aq NH4Cl solution and extracted with ethyl acetate. Purification of the product was effected by chromatography (hept./ethyl acetate) to give 170 mg of 15; $R_f$ 0.47 (hept/ethyl acetate 7/3); NMR (CDCl$_3$) δ4.02, 2.22, 2.09, 1.89 (m, 9, cyclopentane), 2.82, 3.07 (m, 4, CH2CH$_2$), 3.86, 3.93 (s, 6, OCH$_3$).

A solution of 170 mg of 15 in 5 ml of methylenechloride was treated with 250 μl of BBr3. After stirring for 2 hr the reaction was complete. Ice was added and the product extracted with ethyl acetate. Purification was effected by chromatography over silica gel (toluene/ethyl acetate) as eluent, to give 45 mg of 3,9-dihydroxy-7-cyclopentyl-5,6-dihydro-benz[a]anthracene, 16; Mp 233–235° C.; NMR (DMSO) 3.91 (m, 1, CH), 1.75–2.17 (m, 8, cyclopentane), 2.70, 2.97 (m, 2× m, 4, CH$_2$CH$_2$), 9.42, 9.58 (2× s, 2, OH).

A mixture consisting of 200 mg of triflate (12), 76 mg of p-methoxyphenylboronic acid, 26 mg of Pd(PPh$_3$)$_4$, 145 mg of K3PO4 in 3 ml of dioxane was heated for 5 hr at 90° C. at an oil bath . The reaction was diluted with water and extracted with ethyl acetate. The organic material thus obtained was purified by chromatography (hept./ethyl acetate) and provided 162 mg of required 3,9-dimethoxy-7-(4-methoxyphenyl)-5,6-dihydro-benz[a]anthracene, 15a; $R_f$ 0.59 (hept./ethyl acetate 7/3) $R_f$ triflate 0.62; NMR (CDCl$_3$) δ2.70, 2.80 (2× m, 4, CH$_2$CH$_2$), 3.70, 3.85, 3.92 (3× s, 9, OCH3).

To a solution of 162 mg of trimethoxy derivative 15a in 5 ml of methylenechloride was added at –40° C. 0.3 ml of BBr$_3$. The mixture was then stirred at ambient temperature for 3 hr. After pouring into ice water the product was extracted with ethyl acetate and the crude product thus obtained was purified by reversed phase chromatography (silica C18, acetonitrile-water as eluent), to provide 65 mg of crystalline 3,9-dihydroxy-7-(4-hydroxyphenyl)-5,6-dihydro-benz[a]anthracene, 16a; Rf 0.48 (hept./ethyl acetate 4/6), Mp 272° C., NMR (DMSO)) δ2.55 , 2.65 (2× m, 4, CH2CH2), 9.43, 9.45, 9.55 (3× s, 3, OH's).

Example 6

Scheme 10

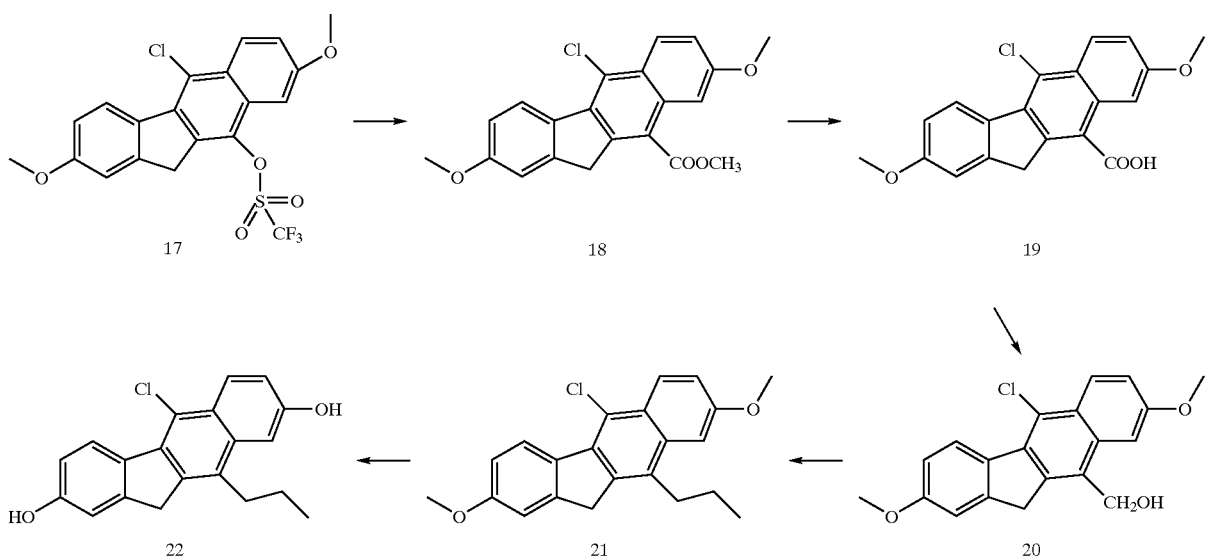

A solution of 680 mg of triflate 17 in a mixture of 10 ml of DMF, 4 ml of methanol, 0.6 ml of triethyl amine, 2 ml of THF and 40 mg of 1,3-bis(diphenylphosphino)propane was flushed with nitrogen for 5 min and then purged with CO for 5 min. To the solution was then added 20 mg of $Pd(OAc)_2$ and the mixture was heated under CO atmosphere (balloon) for 4 hr at 60° C. (an additional portion of catalyst system was added after 1.5 hr). Upon pouring the mixture in water, the products were extracted in ethyl acetate. After drying and concentration, the crude product was finally purified by chromatochraphy over silica gel. This gave 400 mg of 18, Mp 157° C., $R_f$ 0.40 (hept./ethyl acetate 8/2), NMR $(CDCl_3)$ $\delta$3.88, 3.96, 4.10 (3× s, 9, $OCH_3$), 4.25 (s, 2, $CH_2$).

A suspension of 400 mg of 18 in a mixture of 5 ml of dioxane, 2 ml of water and 150 mg of KOH was heated for 2 hr at 100° C. (The mixture became readily a clear solution). The reaction was diluted with water and acidified with 2N HCl. The precipitates were filtered and dried in vacuo, to give 350 mg of carboxylic acid 19; Mp 269–270; $R_f$ 0.40 ($CH_2Cl_2$/methanol 9/1).

To a suspension of 150 mg of 19 in 3 ml of THF was added 0.5 ml of 10M borane.dimethylsulfide. A yellowish precipitate resulted. This was stirred at 45° C. for 1.5 hr. The reaction was carefully diluted with water and extracted with ethyl acetate. The crude product thus obtained was triturated with diisopropylether. This gave 110 mg of alcohol 20 as white solid; Mp 193° C.; NMR (DMSO) 3.85, 3.94 (2× s, 6, $OCH_3$), 4.19 (s, 2, $CH_2$), 4.97 (m, 2, $CH_2OH$), 5.22 (m, 1, OH);. $R_f$ 0.20 (hept/eth.acetate 6/4).

A suspension of 560 mg of alcohol 20 in 4 ml of methylenechloride was treated with 60 mg of triphenylphosphine and then with 75 mg of 1,2-dibromo-1,1,2,2-tetrachloroethane. After stirring for 15 minutes the bromination was complete, and the reaction was worked up by dilution with water and extracion with ethylacetate. The residue which remained after washing, drying and concentration was disolved in 4 ml of dry THF and added to a cuprate solution (prepared by addition of 300 μl of 2.8M ethylmagnesium chloride in THF to a stirred suspension of 60 mg of CuBr and 30 mg of LiCl in in 2 ml of THF at −60° C.). After removing of the cooling the mixture was slowly allowed to come to 0° C. Then the reaction was quenched by addition of sat aq. $NH_4Cl$ solution and extracted with ethyl acetate. Chromatography provided 21 mg of 2,8-dimethoxy-5-chloro-10-propyl-11H-benzo[b]fluorene, 21, as a white solid; Mp 143–145 Rf 0.62 (hept./ethylac. 8/2); NMR $(CDCl_3)$ $\delta$1.08 (s, 3, $CH_3$), 1.78 (m, 2, $CH_2$), 3.07 (m, 2, $CH_2$) 3.90 and 3.97 (2× s, $OCH_3$), 4.03 (s, 2, $CH_2$).

A solution of 20 mg of 21 in 1.5 ml of methylenechloride was treated with 100 μl of $BBr_3$ at −50° C. Mter stirring at ambient temperature for 2 hr the reaction was complete. Ice was added and the product extracted with ethyl acetate. The residue which remained after washing, drying and concentration of the organic phase was treated with a small amount of $CH_2Cl_2$—$CCl_4$ to provide 13 mg of essentially pure 2,8-dihydroxy-5-chloro-10-propyl-11H-benzo[b]fluorene, 22, as a white solid; Mp 223–224; $R_f$ 0.34 (hept./eth. acetate 6/4); NMR (DMSO) $\delta$1.07 (s, 3, $CH_3$),1.68 (m, 2, $CH_2$), 2.87 (m, 2, $CH_2$), 4.02 (s, 2, $CH_2$), 9.72 and 9.87 (2× s, 2, OH's).

Example 6

2,7-dihydroxy-11H-benzo[b]fluorene: 25

Scheme 11

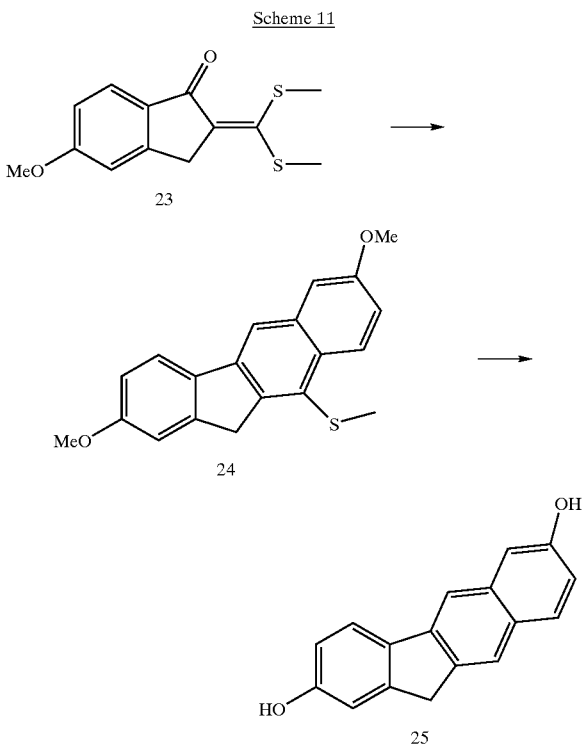

11 ml 3-methoxybenzyl magnesiumchloride (1M in diethyl ether) was added to 23 (7.5 mmol) in 100 ml diethyl ether at 0° C. and the reaction mixture was stirred for 1 hour at 20° C. The mixture was poured into sat. $NH_4Cl(aq)$, extracted with ethyl acetate and dried over $MgSO_4$. After evaporation of the solvent the crude product was purified by chromatography (heptane/ethyl acetate) on silica gel. The pure fractions were combined and concentrated. The resulting product was taken up in 50 ml methanol and treated with $BF_3.Et_2O$ (21 mmol). After 15 minutes the temperature was raised to 60° C. and 1 hour later the reaction mixture was poured into water, extracted with $CH_2Cl_2$ and the organic layer washed with $NaHCO_3$ (aq). The extract was dried over $MgSO_4$, concentrated and the residue was purified on silica gel (heptane/ethyl acetate) affording pure 24 in 34% yield. (Rf=0.54 heptane/ethyl acetate (3:2)). A suspension of 24 (0.22 mmol) and Raney nickel (washed with ethanol, 1 g) in 7 ml ethanol was stirred for 2 hours at 50° C. The Raney nickel was filtered off and the filtrate concentrated. The residue (0.08 mmol) was taken up in 1.5 ml $CH_2Cl_2$ and $BBr_3$ (0.23 mmol) was added. After 2 hours the mixture was carefully poured into sat. $NaHCO_3(aq)$ and extracted with ethyl acetate. The organic layer was dried over $MgSO_4$ and concentrated. Purification on silica (toluene/ethyl acetate) afforded pure 25 in 56% yield.(Rf=0.40 toluene/ethyl acetate (4:1)); ESI-MS: M+H=249.2, M−H=247.0.

Example 8

2,7-dihydroxy-5-chloro-11H-benzo[b]fluorene: 29

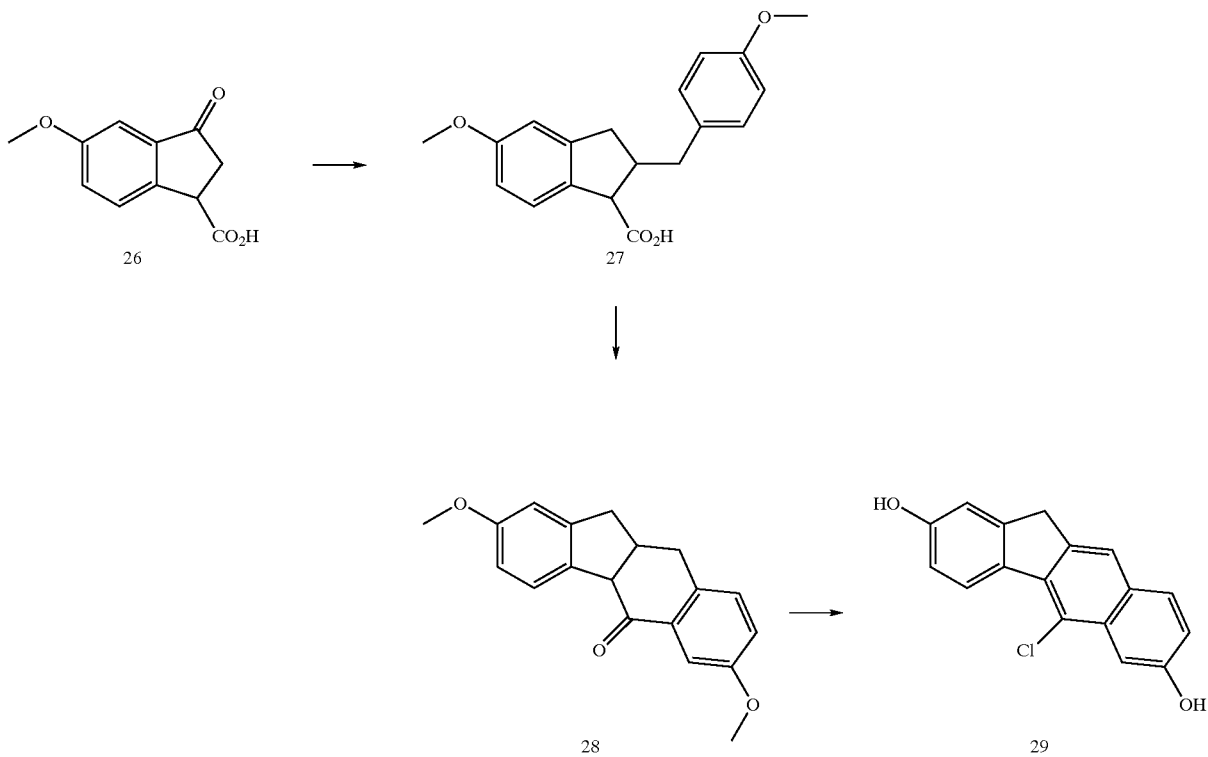

Scheme 12

Compound 27 was prepared in 44% yield, in a similar manner as described for the preparation of compound 26, but using 4-methoxybenzaldehyde instead of 3-methoxybenzaldehyde. (Rf=0.45 toluene/acetone (4:1)); ESI-MS: M+H=313.4, M−H=311.0.

A mixture of 27 (2.8 mmol), TFA (5 ml) and TFAA (5ml) in CH$_2$Cl$_2$ (2 ml) was stirred for 2 hours at 50° C. after which another 5 ml TFA and 5 ml TFAA were added. After 1 hour the mixture was poured into icewater and extracted with ethyl acetate. The organic layer was washed with water, sat. NaHCO$_3$ (aq) and brine. The organic extract was dried over MgSO$_4$ and concentrated. The residue was purified on silica gel (toluene/acetone) to give pure 28 in 56% yield. (Rf=0.83 toluene/acetone (4:1)); ESI-MS: M+H=295.2.

Compound 2,7-dihydroxy-5-chloro-11H-benzo[b] fluorene, 29, was prepared in 5% yield in a similar manner as described for the preparation of compound 60 from 59 (See example 15a). (Rf=0.72 toluene/ethyl acetate (3:2)); ESI-MS: M−H=281.0.

Example 9

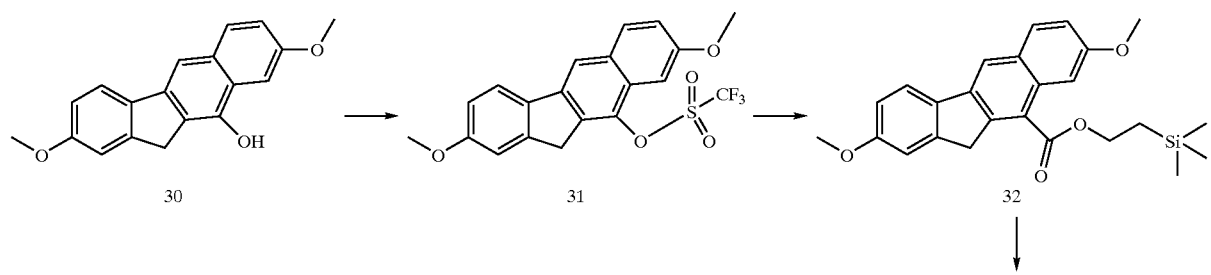

Scheme 13

-continued

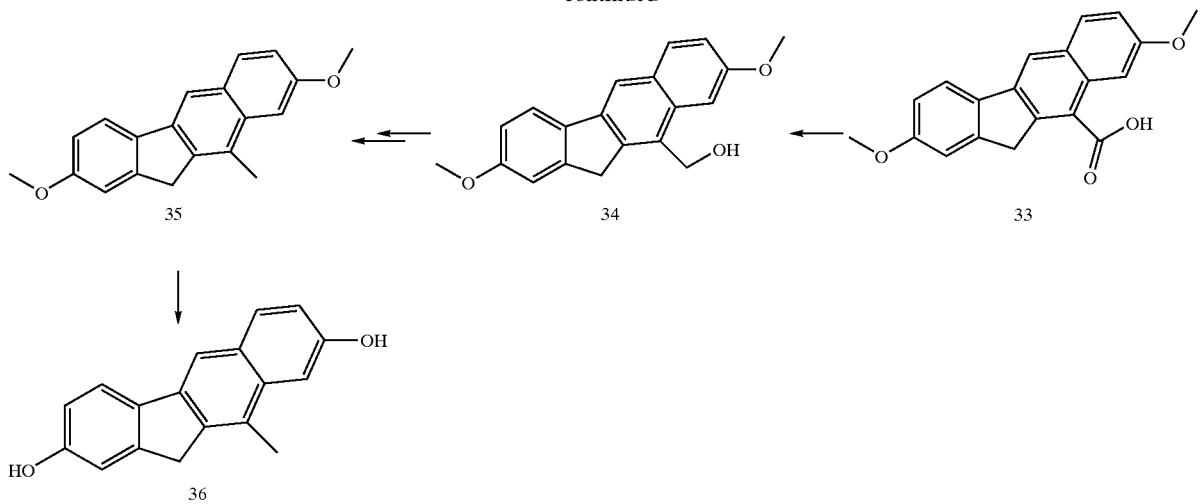

A solution of 300 mg of triflate 31 in a mixture of 4 ml of DMF, 2 ml of 2-trimethylsilylethanol, 0.4 ml of triethyl amine, and 20 mg of 1,3-bis(diphenylphosphino)propane was flushed with nitrogen for 5 min and then purged with CO for 5 min. To the solution was then added 9 mg of Pd(OAc)$_2$ and the mixure was heated under CO atmosphere (balloon) for 2.5 hr at 70° C. (an additional portion of catalyst system was added after 1.5 hr). Upon pouring the mixture in water, the products were extracted in ethyl acetate. After drying and concentration, the remainders of trimethylsilylethanol were removed at the vacuum pump. The product was finally obtained by chromatochraphy over silica gel. This gave 220 mg of 32, solidifying on trituration with heptane; Mp 107–108° C.; NMR(CDCl$_3$) δ 0.15 (s, 9, 3, Si(CH$_3$)), 1.22 (m, 2, CH$_2$), 4.58 (m, 2, CH$_2$); 4.23 (s, 2, CH$_2$), 3.88, 3.95 (2 s, OCH$_3$). R$_f$ 0.71 (tol/eth.ac 95/5).

To a solution of 160 mg of the trimethylsilylethyl ester 32 in 5 ml of THF was added dropwise (!) 0.45 ml of 1 M solution of TBAF in THF. As soon as starting material had disappeared the mixture was quickly diluted with water and acidified with 1N HCl. The product was filtered and dried, to give 105 mg of almost pure carboxylic acid 33, R$_f$ 0.40 (methylenechl/methanol 9/1); NMR (DMSO) δ3.83, 3.89 (2× s, OCH$_3$), 4.21 (s, 2, CH$_2$).

To a solution of 96 mg of carboxylic acid 33 in 3 ml of dry THF was added 150 μl of 10M BMS. After stirring for 4 hr the reduction was complete. The mixture was diluted with water, acidified with 2N HCl and stirred for ½ hr. The resulting alcohol 34 was isolated by filtration from the aquous phase and amounted 80 mg. R$_f$ 0.26 (hept/eth.ac. 6/4), NMR(CDCl3) δ3.83 and 3.87 (2× s, 6, OCH$_3$), 4.21 (s, 2, CH$_2$).

A suspension of 90 mg of alcohol 34 in 4 ml of methylenechloride was treated with 100 mg of triphenylphosphine and then with 130 mg of 1,2-dibromo-1,1,2,2-tetrachloroethane. After stirring for 15 minutes the bromination was complete, and the reaction was worked up by dilution with water and extracion with ethylacetate. The residue which remained after washing, drying and concentration was disolved in 4 ml of dry THF and cooled to −45° C. Then 50 mg of LiAlH$_4$ was added, and then stirred for 20 min at 0° C. The reaction mixture was [poured into water and acidified with 2N HCl. The product was extracted with ethylacetate. Washing, drying and concentration provided 40 mg of essentially pure methyl derivative 2,8-dimethoxy-10-methyl-11H-benzo[b]fluorene, 35; R$_f$ 0.66 (hept/ethylac. 6/4); NMR (CDCl$_3$) δ2.65 (s, 3, CH$_3$), 3.91 and 3.98 (2× s, OCH$_3$), 3.99 (s, 2, CH$_2$).

To a solution of 40 mg of 35 in 5 ml of methylenechloride was added at −25° C. 200 μl BBr$_3$.

The mixture was then stirred at ambient temperature for 2 hr to completion of the reaction. The mixture was quenched by pouring into water and extraction of the product with ethylacetate. The material thus obtained was purified by passing through a short silica column (tol/ethyl ac as eluent) and provided 22 mg of diol 2,8-dihydroxy-10-methyl-11H-benzo[b]fluorene, 36; R$_f$ 0.40 (tol/ethyl ac 7/3); Mp 265° C.; NMR (DMSO d-6) δ9.48, 9.58 (2× s, OH), 2.52 (s, 3, CH$_3$), 3.92 (s, 2, CH$_2$).

Example 10

Scheme 14

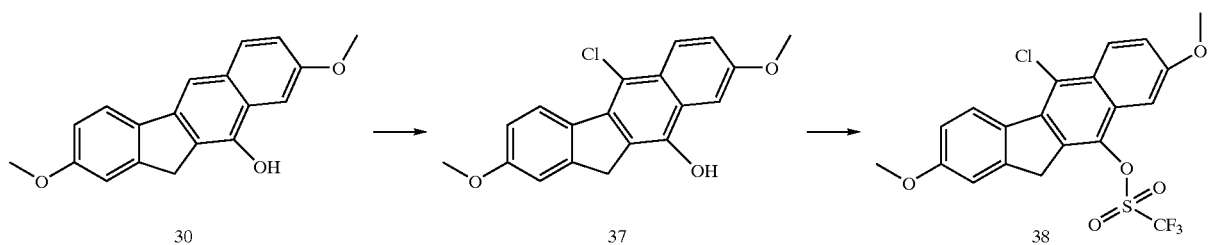

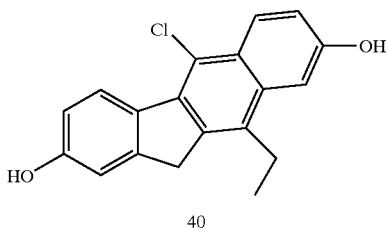

40

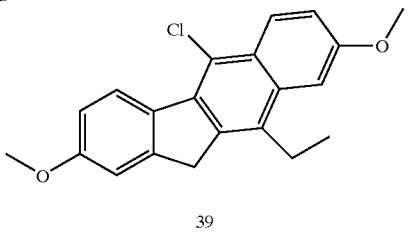

39

To a solution of 2.4 g of phenol 30 in 30 ml of DMF was added at rt in several smaller portions in about 5 min 2.7 g of 2,2,3,4,5,6-hexachlorocycloheha-3,5-dienone. After stirring for ½ h the reaction was complete and the mixture was poured into water and the product extracted with ethyl acetate. Purification af the product by chromatography provided 950 mg of p-chloroderivative 37 as a brown solid; Mp 165–166° C., $R_f$ 0.38 (hept/ethylac. 6/4).

To a solution of 900 mg of chlorophenol 37 in 8 ml of pyridine was added at 0° C. 700 µl of triflicanhydride. The mixture was stirred for an additional two hr at ambient temperature and then poured into water and extracted with ethyl acetate. The crude material was chromatographed over a short silica column, and the material thus obtained was treated with diisopropyl ether, to provide 800 mg of essentially pure triflate 38, Mp 165–168° C., $R_f$ 0.58 (hept/ethyl acetate 8/2); NMR(CDCl$_3$) 19F, −73 ppm triflate, 1H NMR 3.90, 3.98 (2× s,OCH$_3$), 4.18 (s, 2, CH$_2$), A solution of 70 mg of triflate 38 in 3 ml of toluene was charged with 10 mg of NiCl$_2$. DPPE, followed by 120 µl of 2.8M ethylmagnesiumchloride solution in THF). After stirring for two hour the reaction was complete. The materials were poured into 10% aq. NH$_4$Cl and extracted with ethyl acetate. After chromatography over silicagel 36 mg og ethyl derivative 2,8-dimethoxy-5-chloro-10-ethyl-11H-benzo[b] fluorene, 39, remained as a white solid; Mp 163–165° C.; $R_f$ 0.47 (hept/ethylac 8/2). NMR (CDCl$_3$) δ1.35 (t, 3, CH$_3$), 3.10 (q, 2, CH$_2$), 4.02 (s, 2, CH$_2$), 3.90, 3.98 (2× s, 6, OCH$_3$).

To a solution of 25 mg of 39 in 3 ml of methylenechloride was added at −25° C. 100 µl BBr$_3$.

The mixture was then stirred at ambient temperature for 2 hr to completion of the reaction. The mixture was quenched by pouring into water and extraction of the product with ethylacetate. The material thus obtained was purified by passing through a short silica column (tol/ethyl ac. as eluent) and provided 22 mg of diol 2,8-dihydroxy-5-chloro-10-ethyl-11H-benzo[b]fluorene, 40; $R_f$ 0.36 (hept/ethyl ac 6/4); Mp 250–251° C.; NMR (DMSO d-6) δ9.75, 9.90(2× s, OH), 1.25 (t, 3, CH$_3$), 3.00 (q, 2, CH$_2$), 4.02 (s, 2, CH$_2$)

Example 11

Scheme 15

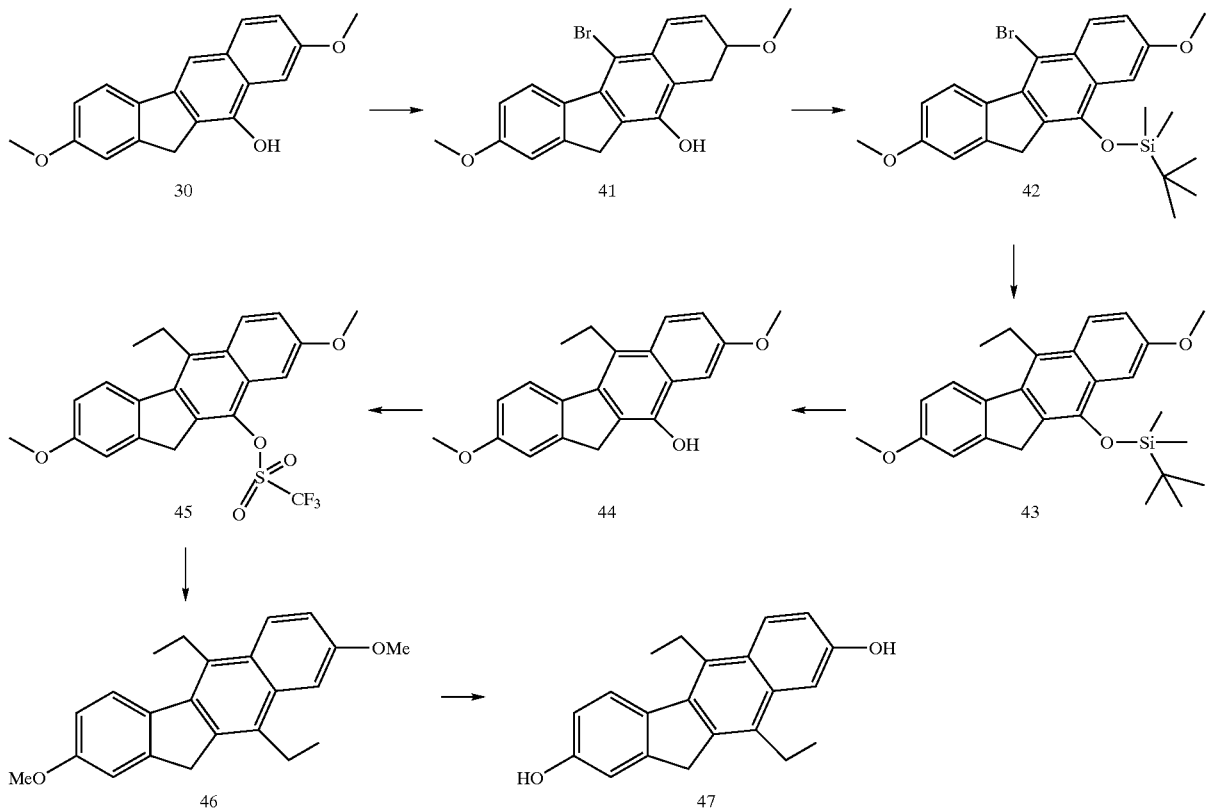

To a suspension of 1 gr of phenol 30 in 10 ml of acetonitrile was added in small portions at rt 600 mg of NBS. After 1 h the bromination was completed. The mixture was poured into water and the dark brown material was filtered, and triturated with 80% aq ethanol, to give after vacuo drying at 50° C. 1.1 g of crude 41. This was dissolved in 5 ml of DMF and 0.5 g of imidazole and 0.6 g of tBDMSCl were succesively added at 0° C. The reaction was stirred for 1 hr and then poured onto water and extracted with ether. The material thus obtained was purified by chromatography and triturated with 90% aq. ethanol to yield 1.1 g of silylated product 42; Mp 134–135° C.; $R_f$ 0.48 (hept/ethyl ac 9/1); NMR (CDCl$_3$) δ0.28 (s, 2, Si(CH$_3$)$_2$)1.15 (s,9,Sit$_4$H$_9$), 3.90 and 3.95 (2× s, 6, OCH$_3$). 4.00 (s, 2, CH$_2$).

To a mixture containing 200 mg of bromide 42, and 30 mg of NiCl$_2$.DPPP in 5 ml of toluene under N$_2$atmosphere was added 300 μl of 2.8M ethylmagnesium chloride solution (in THF)

After stirring for 2 hr the reaction was complete. The mixture was diluted with 10% aq. NH4Cl solution and extracted with ethyl acetate. The crude material thus obtained was purified from the reduction product by silica gel chromatography, to give 55 mg of ethyl product 43, Mp 118–120° C.; $R_f$ 0.50 (hept./ethyl acetate 9/1). NMR(CDCl$_3$) δ1.40 (t, 3, CH$_3$), 3.42 (q, 2, CH$_2$), 0.28 (s, 6, Si(CH$_3$)$_2$), 1.18 (s, 9,Si tC$_4$H$_9$), 4.00 (s, 2, CH$_2$), 3.90 and 3.95 (2× s, 6, OCH$_3$). Reduction product $R_f$ 0.45.

To 320 mg of silylether 14 in 3 ml of dry THP was added 1 ml of 1M TBAF in THF. After stirring for 15 min the mixture was diluted with water and slightly acidified with 1N HCl. The product was extracted with ethyl acetate. After concentration of the organic phase the residue was treated with diisopropylether/heptane (1/1) to give 190 mg of a brownish solid phenol 44; $R_f$ 0.29 (hept/ethyl acetate 7/3).

This matyerial was dissolved in 2 ml of pyridine and treated with 200 μl of triflic anhydride. After stirring for 1.5 h the reaction was complete. Ice water was added and the product extracted into ethylacetate. After chromatography 190 mg of triflate 45 were isolated; Mp 199–200° C. $R_f$ 0.67 (hept./ethyl ac. 7/3);

NMR (CDCl$_3$) δ1.42 (t, 3, CH$_3$), 3.47(q, 2, CH$_2$), 4.19 (s, 2, CH$_2$) ; −74 ppm $^{19}$F resonance.

To a mixture containing 140 mg of triflate 45, and 30 mg of NiCl$_2$.DPPP in 5 ml of toluene under N$_2$atmosphere was added 350 μl of 2.8M ethylmagnesium chloride solution (inTHF). The mixture was stirred for ½ hr at 45° C. Then sat aq NH$_4$Cl was added and the products extracted with ethyl acetate. Chromatography provided 110 mg of 2,8-dimethoxy-5,10-diethyl-11H-benzo[b]fluorene, 46; Mp 155–157° C., $R_f$ 0.46 (hept/ethyl acetate 9/1) 0.46. NMR (CDCl$_3$) δ1.37 and 1.45 (2×t, 6, CH$_3$), 3.12 and 3.47(2×q, 4, CH$_2$), 4.01 (s, 2, CH$_2$).

To a solution of 100 mg of 46 in 3 ml of methylenechloride was added at −25° C. 300 μl BBr$_3$.

The mixture was then stirred at ambient temperature for 1 hr to completion of the reaction. The mixture was quenched by pouring into water and extraction of the product with ethylacetate. The material thus obtained was purified treatment with hot ethyl acetate and provided 48 mg of diol 2,8-dihydroxy-5,10-diethyl-11H-benzo[b]fluorene, 47; $R_f$ 0.60 (tol/ethyl ac 7/3); Mp 255° C. (dec); NMR (DMSO d-6) δ9.53, and 9.59(2× s, OH), 1.25 and 1.30 (2× t, 3, CH$_3$), 3.00 and 3.37 (2× q, 2, CH$_2$), 3.95 (s, 2, CH$_2$).

Example 12

Scheme 16

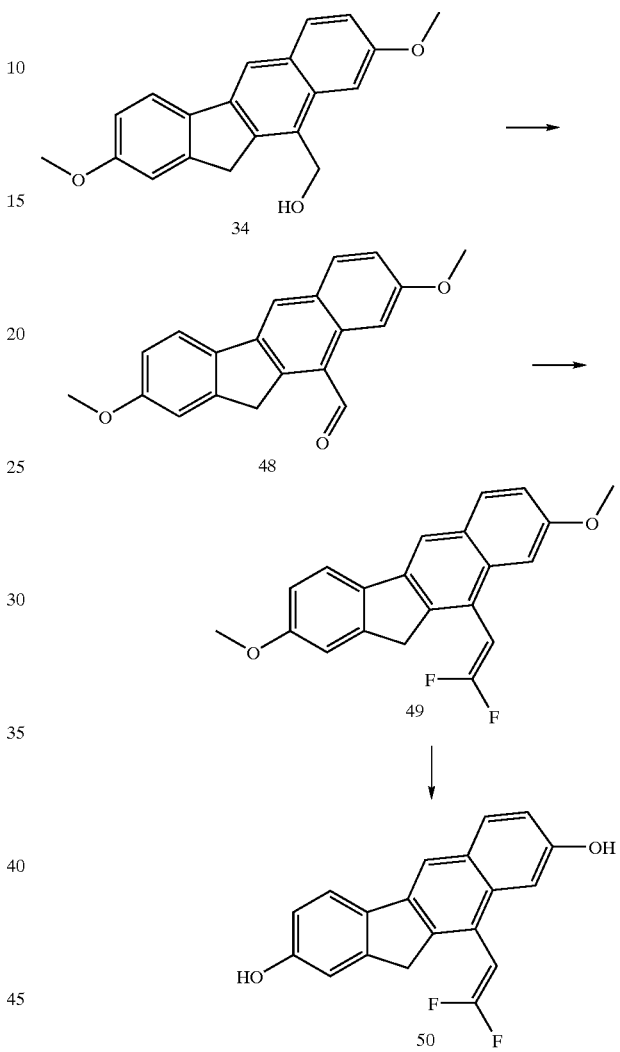

To a solution of 670 mg of alcohol 34 in 90 ml of methylenechloride was added 2,3 g of pyridiniumchlorochromate, 1.8 g of sodiumacetate and 4 g of silicagel. The mixture was stirred for 3 hr until completion of the reaction. The mixture was then filtered over Celite and concentrated, and the residue purified by filtration over silicagel (hept./ethyl acetate) to give 600 mg of aldehyde 48. NMR (CDCl$_3$) δ10.95 (s, 1, CHO), 3.92, 4.00 (2× s, OCH$_3$), 4.40 (s, 2, CH$_2$). $R_f$ 0.56 (hept/ethyl acetate 6/4).

A solution of lithiumdiisoprpylamide was prepared by addition of 0.3 ml of 1.6M BuLi-heptane to 0.73 μl of diisopropylamine in 3 ml of dry THF at −60° C. To this solution was then added 133 mg of diphenyldifluoromethylphosphinoxde in 3 ml of THF. After stirring for 30 min. at −60° C. a solution of 100 mg of aldehyde 48 in 2 ml of THF was added and the cooling device was removed and the mixture was then stirred for an additional 3 hr at ambient temperature. The reaction was quenched by addition of water, followed by extraction of the product with ethylacetate. After passing through a silica column (hept/ethyl acetate as eluent) 90 mg of 2,8-dimethoxy-10-(2,2-difluoro-ethenyl)-11H-benzo[b]fluorene, 49, was obtained; Mp 82–85° C.; $R_f$ 0.63 (hept/ethyl acetate 7/3). NMR (CDC$_3$) δ5.70 (d, CHCF$_2$), 3.97 (s,2,CH$_2$), 3.90, and 3.97 (2× s, OCH$_3$).

To a solution of 60 mg of 49 in 4 ml of methylenechloride was added at –20° C. 100 µl of BBr$_3$. The mixture was then stirred at ambient temperature for 3 hr, until completion of the reaction. Then ice water was added followed by extraction of the product with ethyl acetate. After passing through a short silica column (hept./ethyl acetate as eluent) the purified material was treated with 90% ethanol, to give 35 mg of 2,8-dihydroxy-10-(2,2-difluoro-ethenyl)-11H-benzo[b]fluorene, 50, Mp 211–212° C., $R_f$ 0.16 (hept./ethy ac. 6/4). NMR (DMSO d6) 9.55 and 9.72 (2× s, 2, OH), 6.12 (d, 1, CHCF$_2$), $^{19}$F NMR –82 and –86 ppm, fluoro resonances.

Example 13

Scheme 17

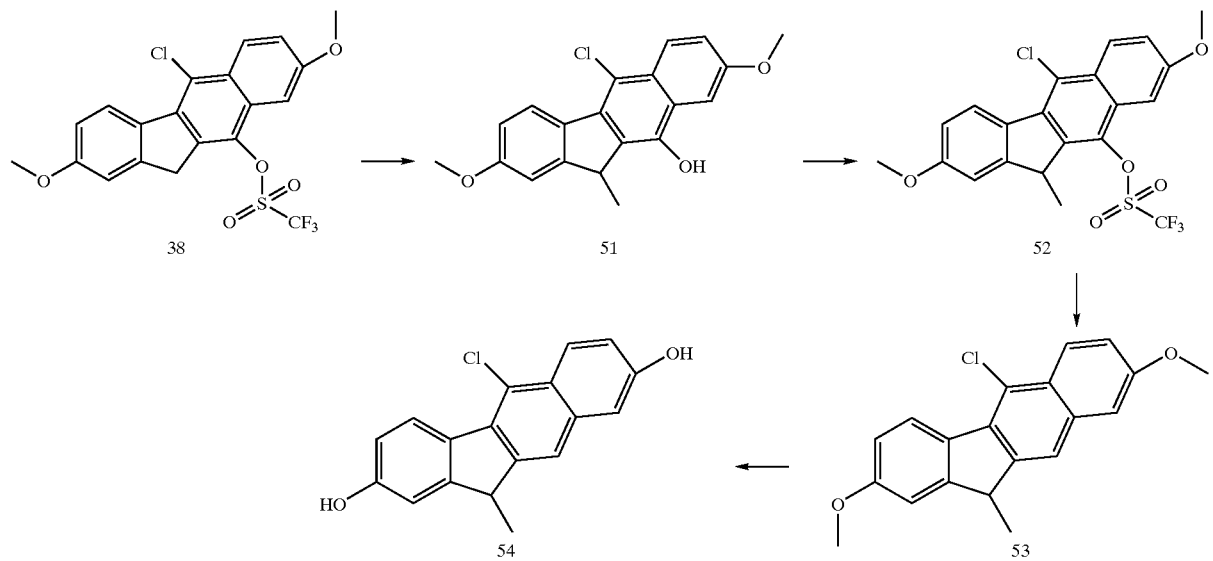

To a mixture containing 200 mg of triflate 38, and 30 mg of NiCl$_2$.DPPE in 5 ml of toluene under N2atmosphere was added 350 µl of 2.8M methylmagnesium chloride solution (inTHF).

After stirring for 2 hr at 50° C. the reaction was complete. The mixture was diluted with 10% aq. NH$_4$Cl solution and extracted with ethyl acetate. The crude material thus obtained was purified by silica gel chromatography, to give 100 mg of product 51, as a dark foam; $R_f$ 0.420 (hept./ethyl acetate 6/4). NMR (DMSO) δ9.65 (s, 1, OH), 4.28 (m, 1, CH) 3.85, 3.92 (2× s, 6, OCH$_3$), 1.52 (d, 3, CH$_3$).

To a solution of 60 mg of chlorophenol 51 in 1 ml of pyridine was added at 0° C. 100 µl of triflicanhydride. The mixture was stirred for an additional two hr at ambient temperature and then poured into water and extracted with ethyl acetate. The crude material was chromatographed over a short silica column, and the material thus obtained was treated with diisopropyl ether, to provide 52 mg of essentially pure triflate 52, Mp 149–150° C., $R_f$ 0.66 (hept/ethyl acetate 8/2); NMR 19F, (CDCl$_3$) –74 ppm triflate, NMR (CDC$_3$) δ3.91, 3.97 (2× s,6, OCH$_3$), 4.48 (m, 1, CH), 1.62 (d, 3, CH$_3$).

To a mixture containing 50 mg of triflate 52, and 10 mg of NiCl$_2$.DPPE in 2 ml of toluene under N$_2$atmosphere was added 150 µl of 2.8M ethylmagnesium chloride solution (in THF)

After stirring for ½ hr at 50° C. the reaction was complete. The mixture was diluted with 10% aq. NH₄Cl solution and extracted with ethyl acetate. The crude material thus obtained was purified by silica gel chromatography, to give 23 mg of 2,8-dimethoxy-5-chloro-11-methyl-11H-benzo[b] fluorene, 53; R$_f$ 0.47 (hept./ethyl acetate 8/2). NMR(CDCl₃) δ 4.10 (m, 1, CH) 3.90, 3.95 (2× s, 6, OCH₃), 1.59 (d, 3, CH₃).

To a solution of 21 mg of 53 in 1.4 ml of methylenechloride was added at −20° C. 100 μl of BBr₃. The mixture was then stirred at ambient temperature for 1 hr, until completion of the reaction. Then ice water was added followed by extraction of the product with ethyl acetate. After passing through a short silica column (tol./ethyl acetate as eluent) the purified material was treated with ethanol/water, to give 12 mg of 2,8-dihydroxy-5-chloro-11-methyl-11H-benzo[b] fluorene, 54, Mp 215–220° C., R$_f$ 0.45 (tol./ethy ac. 7/3). NMR (DMSO d6) 9.78 and 9.90 (2× s, 2, OH), 4.05 (m, 1, CH), 1.50 (d, 3, CH₃).

Example 14

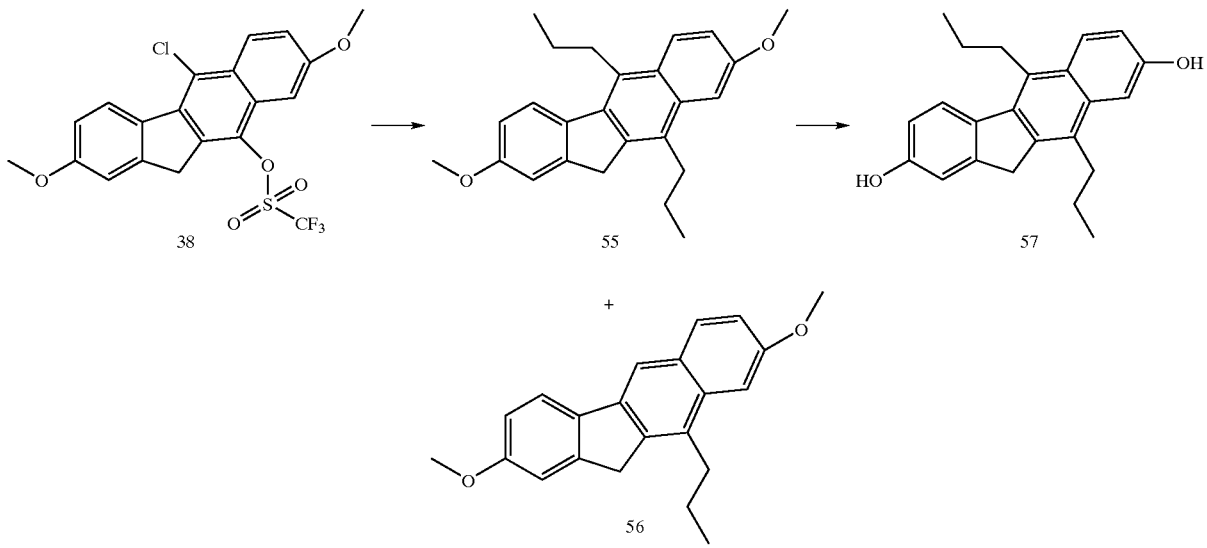

Scheme 18

Triflate 38 (240 mg) was mixed with 6 ml of dry toluene and 50 mg of NiCl2.DPPE complex and flushed with nitrogen. Then 1 ml of a solution of 2 M propylmagnesiumchloride—ether was added and stirring continued for 2 hr, until disappearance of the starting material. The mixture was then poured into sat. NH₄Cl solution and extracted with ethyl acetate. The products 2,8-dimethoxy-5,10-dipropyl-11H-benzo[b]fluorene, 55, and 2,8-dimethoxy-10-propyl-11H-benzo[b]fluorene, 56, thus obtained were separated by chromatography (heptane/ethylacetate 98/2 as eluent), to provide 70 mg of dipropyl derivative 55 as well as 65 mg of monopropyl derivative 56; Mp (55) 145–147° C., Mp (56) 130–132° C. R$_f$ (55) 0.65 (heptane/ethylacetate 8/2); R$_f$ (56) 0.60. NMR (CDCl₃) δ(55) 1.10 and 1.21 (2× t, 6, CH₃), 1.80 (m,4, 2×CH₂), 3.07 and 3.39 (2× m, 4, CH₂), 3.90 and 3.97 (2× s, 6, OCH₃), 4.01 (s, 2, CH₂) NMR(CDCl₃) δ(56) 1.08 (t, 3, CH₃), 1.80 and 3.10 (2× m, 4, CH₂), 3.89 and 3.97 (2× s, 6, OCH₃), 3.99 (s, 2, CH₂).

To a solution of 65 mg of 55 in 4 ml of methylenechloride was added at −20° C. 250 μl of BBr₃. The mixture was then stirred at ambient temperature for 2 hr, until completion of the reaction. Then ice water was added followed by extraction of the product with ethyl acetate. The product which remained after washing, drying and concentration was triturated with diisopropylether to give 35 mg of white solid 2,8-dihydroxy-5,10-dipropyl-11H-benzo[b]fluorene, 57; R$_f$ 0.47 (hept./ethyl acetate 6/4); Mp. 250° C.; NMR (DMSO) 1.05 and 1.15 (2×t, 6, CH₃), 1.66 (m, 4, 2×CH₂), 2.94 and 3.28 (2× m, 4, CH₂), 3.93 (s, 2, CH₂), 9:56 and 9.53 (2× s, 2, OH's).

Example 15

Scheme 19

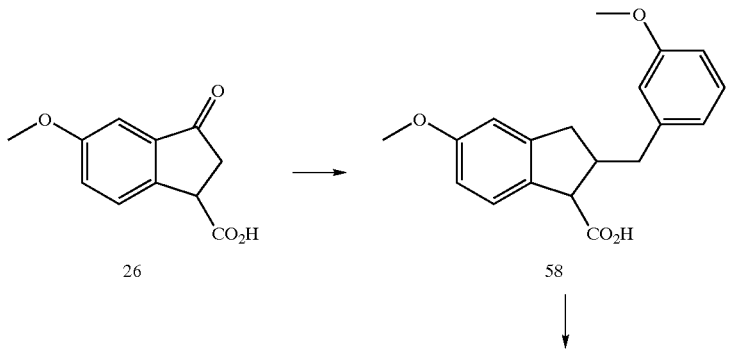

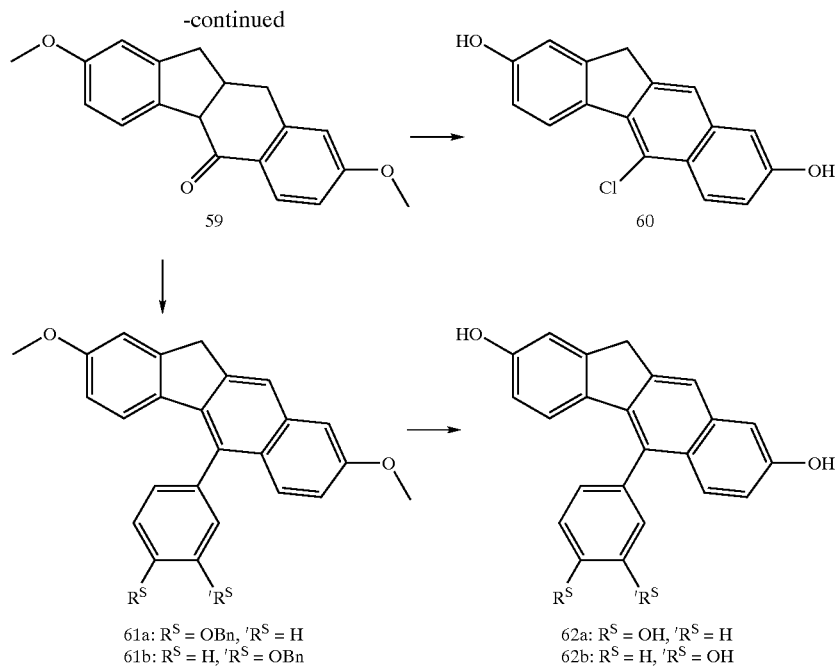

61a: $R^S$ = OBn, $'R^S$ = H
61b: $R^S$ = H, $'R^S$ = OBn

62a: $R^S$ = OH, $'R^S$ = H
62b: $R^S$ = H, $'R^S$ = OH

Example 15a 2,8-dihydroxy-5-chloro-11H-benzo[b]fluorene: 60

A mixture of 26 [Chiu, C. K-F. et al, Aust. J. Chem., 45, 1, 227–248 (1992)] (46 mmol), KOtBu (98 mmol) and 3-methoxybenzaldehyde (68 mmol) in 200 ml methanol was stirred at 50° C. After 2 hours water was added and the mixture was acidified with 2 N HCl. The solid was collected by filtration and recristallised from toluene/heptane.

A mixture of these crystals and palladium on charcoal (10% w/w, 3 g) in 800 ml ethyl acetate/methanol (3:1) was stirred under 30 psi of hydrogen for 5.5 hours. The catalyst was removed by filtration and the filtrate was concentrated to give 58 in 93% yield. (Rf=0.49 toluene/acetone (4:1)), ESI-MS: M−H=311.

A solution of 58 (40 mmol) in 250 ml methanesulfonic acid was stirred overnight at RT, poured into ice water and extracted with $CH_2Cl_2$. The organic extract was washed with sat. $NaHCO_3$(aq), dried over $MgSO_4$ and concentrated. Chromatography on silica gel (toluene/ethyl acetate) gave pure 59 in 62% yield. (Rf=0.80 toluene/acetone (4:1)).

To a solution of 59 (0.19 mmol) in toluene (2.5 ml) was added $PCl_5$ (1.3 mmol). After stirring the mixture for 1 hour at 20° C. it was poured into water and extracted with toluene. The organic layer was washed with sat. $NaHCO_3$ (aq), dried over $MgSO_4$, concentrated and purified on silica gel (heptane/ethyl acetate). The purified product was dissolved in $CH_2Cl_2$ (2 ml) and $BBr_3$ (0.4 mmol) was added. After 2 hours the mixture was carefully poured into sat. $NaHCO_3$ (aq) and extracted with ethyl acetate. The organic layer was dried over $MgSO_4$ and concentrated. Purification on silica gel (toluene/ethyl acetate) afforded pure 60 in 53% yield. (Rf=0.26 toluene/ethyl acetate (4:1)); ESI-MS: M+H=283.0, M−H=281.0.

Example 15b 2,8-dihydroxy-5-(4-hydroxyphenyl)-11H-henzo[b]fluorene: 62a 4-(Benzyloxy) phenyl lithium (1 mmol) (prepared from 4-(benzyloxy) phenyl bromide and butyl lithium at −30° C.) was added to 59 (0.68 mmol) in THF (4 ml) at −30° C. and the temperature was raised to RT over 1 hour. The mixture was poured into sat. $NH_4Cl$ (aq), extracted with ethyl acetate, dried over $MgSO_4$ and concentrated. The residue was taken up in acetone (20 ml), p-toluenesulfonic acid (29 mg) was added and the mixture was stirred overnight at RT. Water was added and the mixture was extracted with ethyl acetate. The organic extract wa washed with sat. $NaHCO_3$ (aq), dried over $MgSO_4$ and concentrated. Purification on silica gel (heptane/ethyl acetate) afforded pure 2,8-dimethoxy-5-(4-benzyloxyphenyl)-11H-benzo[b]fluorene, 61a, in 18% yield. (Rf=0.61 heptane/ethyl acetate (4:1)); ESI-MS: M+H=461.2.

A mixture of 61a (0.11 mmol) and palladium on charcoal (10% w/w, 100 mg) in m-xylene (5 ml) was heated at 125° C. for 1 hour. After the mixture had cooled ethanol (20 ml) was added and the mixture was stirred under an atmosphere of hydrogen for 1 hour. The catalyst was removed by filtration, the filtrate was 35 concentrated and purified by chromatography on silica gel (toluene/ethyl acetate). The purified product was dissolved in $CH_2Cl_2$ and boron trifluoride-methyl sulfide complex (0.86 mmol) was added. The mixture was stirred overnight at RT, poured into sat. $NaHCO_3$ (aq) and extracted with ethyl acetate. The organic layer was dried over $MgSO_4$ and concentrated. Purification on silica ($CH_2Cl_2$/methanol) afforded pure 62a in 40% yield. (Rf=0.25 $CH_2Cl_2$/methanol (9:1)); ESI-MS: M−H=339.0.

Example 15c 2,8-dihydroxy-5-(3-hydroxyphenyl)-11H-benzo[b]fluorene: 62b

Compound 62b was prepared from 2,8-dimethoxy-5-(3-benzyloxyphenyl)-11H-benzo[b]fluorene, 61b, in 14% yield, in the same fashion as described for the preparation of 62a, but using 3-(benzyloxy) phenyl lithium instead of 4-(benzyloxy) phenyl lithium (Rf<0.26 $CH_2Cl_2$/methanol (9:1)); ESI-MS: M+H=341.2, M−H=339.0.

Example 16

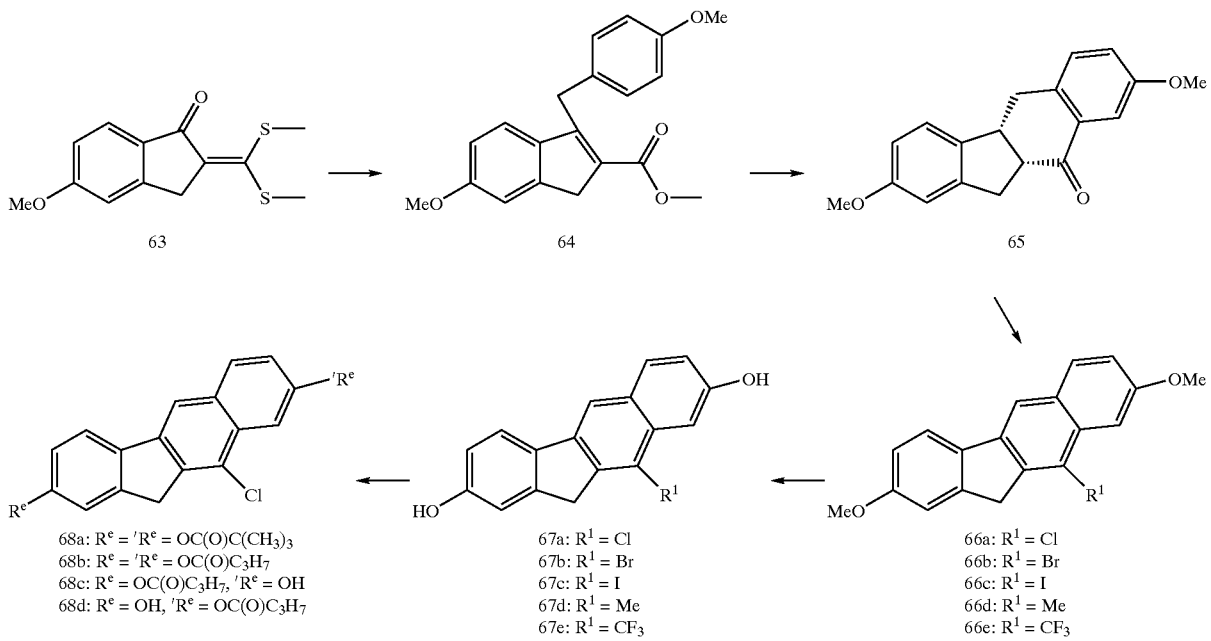

68a: $R^e$ = $'R^e$ = $OC(O)C(CH_3)_3$
68b: $R^e$ = $'R^e$ = $OC(O)C_3H_7$
68c: $R^e$ = $OC(O)C_3H_7$, $'R^e$ = OH
68d: $R^e$ = OH, $'R^e$ = $OC(O)C_3H_7$

67a: $R^1$ = Cl
67b: $R^1$ = Br
67c: $R^1$ = I
67d: $R^1$ = Me
67e: $R^1$ = $CF_3$

66a: $R^1$ = Cl
66b: $R^1$ = Br
66c: $R^1$ = I
66d: $R^1$ = Me
66e: $R^1$ = $CF_3$

Example 16a 2,8-dihydroxy-10-chloro-11H-benzo[b]fluorene: 67a 59 ml 4-methoxybenzyl-magnesium chloride (0.2 M in diethyl ether) was added to 63 [J. V. Ram and M. Nath, *Indian J. Chem*. Sect.B; 34, 416–422 (1995)] (11.6 mmol) in 70 ml THF at 0° C. and the reaction mixture was stirred for 0.5 hour at 20° C. The mixture was poured into saturated aq. $NH_4Cl$, extracted with diethyl ether and dried over $MgSO_4$. After evaporation of the solvent the crude product was purified by chromatography on silica gel (heptane/ethyl acetate). The pure fractions were concentrated and the material obtained was taken up in 95 ml methanol and treated with $BF_3.Et_2O$ (28 mmol). After 0.5 hour the temperature was raised to 65° C. and after 0.5 hour the reaction mixture was poured into water, extracted with $CH_2Cl_{12}$ and the organic layer washed with $NaHCO_3$ (aq). The extract was dried over $MgSO_4$, concentrated and the residue was recrystallised from methanol to afford pure 64 in 45% yield (Rf=0.48 heptane/ethyl acetate (3:2)).

A mixture of 64 (5 mmol) and palladium on carbon (10% Pd (w/w), 300 mg) in 120 ml ethanol/acetic acid (5:1) was stirred under an atmosphere of hydrogen for 1 hour. The catalyst was removed by filtration and the filtrate was concentrated.

The residue was dissolved in methanesulfonic acid and stirred at 90° C. for 15 minutes after which the mixture was poured into ice water and extracted with ethyl acetate. The organic layer was washed with $NaHCO_3$(aq) and dried over $MgSO_4$. Chromatography on silica gel (heptane/ethyl acetate) gave pure 65 in 85% yield. (Rf=0.49 heptane/ethyl acetate (2:1))

To a solution of 65 (0.8 mmol) in toluene (8 ml) was added $PCl_5$ (4.8 mmol). After stirring the mixture for 2 hours at 20° C. it was poured into ice water and extracted with toluene. The organic layer was washed with $NaHCO_3$ (aq), dried over $MgSO_4$ and concentrated. The residue was dissolved in 12 ml m-xylene/toluene (2:1) palladium on carbon (10% w/w, 200 mg) was added and the mixture was refluxed for 2 hours. The catalyst was filtered off and the filtrate was concentrated. Chromatography (heptane/ethyl acetate) gave pure 2,8-dimethoxy-10-chloro-11H-benzo[b]fluorene 66a in 92% yield. (Rf=0.58 heptane/toluene (1:1)) $BBr_3$ (3.5 mmol) was added to a solution of 66a (1.18 mmol) in 30 ml $CH_2Cl_2$ and after 1 hour another 2.1 mmol of $BBr_3$ was added. After 1.5 hours the mixture was carefully poured into sat. $NaHCO_3$ (aq) and extracted with ethyl acetate. The organic layer was dried over $MgSO_4$ and concentrated. Purification on silica (toluene/ethyl acetate) afforded pure 67a in 87% yield. (Rf=0.38 toluene/ethyl acetate (4:1)); ESI-MS: M+H= 283.0, M−H=281.2.

Example 16b 2,8-dihydroxy-10-bromo-11H-benzo[b]fluorene; 67b

A mixture of 500 mg $POBr_3$ and 0.34 mmol 65 was heated for 1 hour at 90° C. and 1 hour at 120° C. after which the mixture was poured into water and extracted with ethyl acetate. The organic layer was washed with sat. $NaHCO_3$ (aq), dried over $MgSO_4$ and concentrated. The residue was purified on silica gel (heptane/ethyl acetate). The resulting bromide was treated with 100 mg palladium on carbon (10% w/w) in 2 ml m-xylene at 125° C. for 2 hours. The catalyst was removed by filtration and the filtrate concentrated to give pure 2,8-dimethoxy-10-bromo-11H-benzo[b]fluorene, 66b, in 19% yield. (Rf=0.50 heptane/toluene (1:1)). Compound 67b was obtained in 92% yield in the same fashion as described for the conversion of 66a to 67a. (Rf=0.52 toluene/ethyl acetate (7:3)); ESI-MS: M−H=325.0+327.0 (1:1).

Example 16c 2,8-dihydroxy-10-iodo-11H-benzo[b]fluorene: 67c 65 (0.34 mmol) was dissolved in ethanol and 1 ml hydrazine monohydrate was added. After 4 hours refluxing, water was added and the hydrazone was extracted with $CH_2Cl_2$. The organic layer was washed with water, dried and concentrated. The residue was taken up in 1.5 ml triethylamine and 0.2 g iodine in 0.7 ml THF was added at 0° C. After 1 hour the reaction mixture was diluted with toluene, poured into ice water and extracted with toluene. The organic layer was washed with 1N HCl and saturated $NaHCO_3(aq)$, dried over $MgSO_4$ and concentrated. The residue was dissolved in 8 ml m-xylene/toluene (2:1) palladium on carbon (10% w/w, 100 mg) was added and the mixture was heated at 125° C. for 2 hours. After cooling the catalyst was filtered off, the filtrate was concentrated and the residue was purified on silica (heptane/ethyl acetate) to give pure 2,8-dimethoxy-10-iodo-11H-benzo[b]fluorene: 66c in 41% yield. (Rf=0.58 (heptane/ethyl acetate (4:1)).

66c was demethylated in a similar manner as described for the conversion of 66a to 67a to give pure 67c in 62% yield. (Rf=0.50 toluene/ethyl acetate (4:1)); ESI-MS: M+H=375.2, M−H=373.0.

Example 16d 2,8-dihydroxy-10-methyl-11H-benzo[b]fluorene: 67d 65 (0.34 mmol) was dissolved in 5 ml dry diethyl ether and 0.13 ml methyl magnesium chloride (22%, w/w) in THF) was added. After 2 hours water was added and the mixture was extracted with diethyl ether. The organic layer was dried over $MgSO_4$, concentrated and the residue was purified on silica gel (toluene/ethyl acetate). The alcohol was taken up in 5 ml acetone and 4 mg p-toluenesulfonic acid was added. After 3 hours water was added and the mixture was extracted with ethyl acetate. The organic layer was washed with $NaHCO_3(aq)$, dried over $MgSO_4$, concentrated and the residue was purified on silica gel (heptane/ethyl acetate). The purified product was treated with 20 mg palladium on carbon (10% w/w) in 3 ml m-xylene/toluene (2:1) at 125° C. for 2 hours. The catalyst was removed by filtration and the filtrate was concentrated. The residue was chromatographed on silica gel (heptane/ethyl acetate) to give pure 2,8-dimethoxy-10-methyl-11H-benzo[b]fluorene, 66d, in 15% yield. (Rf=0.67 toluene/ethyl acetate (3:2)).

66d was demethylated in a similar manner as described for the conversion of 66a to 66a to give pure 67d in 51% yield.(Rf=0.22 toluene/ethyl acetate (3:2)).

Example 16e 2,8-dihydroxy-10-trifluoromethyl-11H-benzo[b]fluorene: 67e 65 (0.51 mmol) was dissolved in 2 ml dry THF. Trifluoromethyl trimethylsilane (0.15 ml) was added and the mixture was cooled to −20° C. Tetrabutylammonium fluoride in THF (0.3 ml) was added and the temperature was raised to 0° C. After 2 hours another 0.35 ml Trifluoromethyl trimethylsilane was added at 0° C. and the temperature was raised to 20° C. After 16 hours water was added and the mixture was extracted with ethyl acetate. The organic layer was concentrated and the residue was chromatographed on silica gel (toluene/ethyl acetate). The alcohol and 2 mg p-toluenesulfonic acid were taken up in 2 ml toluene and refluxed for 3 hours after which water was added. The mixture was extracted with toluene, the organic layer was concentrated and purified on silica gel (toluene/ethyl acetate). The purified product was treated with 20 mg palladium on carbon (10%, w/w) in 3 ml m-xylene at 125° C. for 24 hours. The catalyst was removed by filtration and the filtrate concentrated to give pure 2,8-dimethoxy-10-trifluoromethyl-11H-benzo[b]fluorene, 66e, in 9% yield. (Rf=0.77 toluene/ethyl acetate (3:2)). 66e was deprotected in a similar manner as 66a to give pure 67e in 21% yield.(Rf=0.32 toluene/ethyl acetate (7:3)).

Example 16f di-pivaloyl Ester of 2,8-dihydroxy-10-chloro-11H-benzo[b]fluorene: 68a 67a (1.8 mmol) was taken up in 15 ml of pyridine and pivaloyl chloride (5.4 mmol) was added. After 2 hours water was added and the white precipitate was collected by filtration. The precipitate was purified on silica gel (heptane/toluene) to give pure 68a in 73% yield. (Rf=0.81 (heptane/ethyl acetate (3:2); $^1$H-NMR: δ=1.40 ppm (s, 9H), 1.43 ppm (s, 9H), 4.01 ppm (s, 2H).

Example 16g

Mono and Dibutyryl Esters of 2,8-dihydroxy-10-chloro-11H-benzo[b]fluorene: 68b, 68c and 68d 67a (1.0 mmol) was taken up in 22 ml of pyridine and butyryl chloride (1.0 mmol) was added. After 1 hour another 0.55 mmol of butyryl chloride was added. After another 1.5 hours water was added and the mixture was extracted with ethyl acetate. The organic layer was dried over $MgSO_4$ and concentrated. The residue was chromatographed on silica gel (heptane/ethyl acetate) to give pure 68b in 51% yield (Rf=0.68), 68c in 14% yield (Rf=0.43) and 68d in 16% yield (Rf=0.39 heptane/ethyl acetate (3:2)).

Example 17

2,8-dihydroxy-11H-benzo[b]fluorene: 69

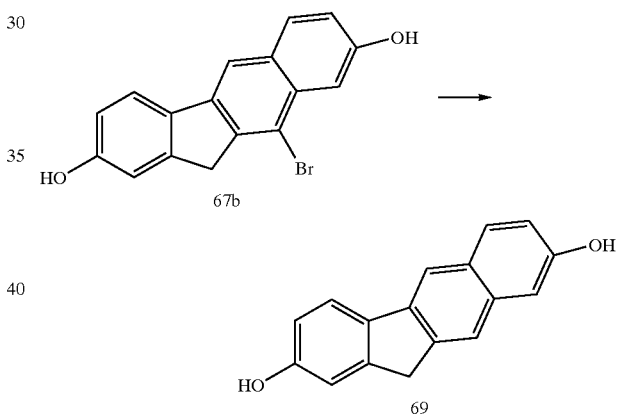

Scheme 21

A mixture of 67b and palladium on carbon (10% w/w, 20 mg) in 2 ml ethanol was stirred under 25 psi of hydrogen for 7 hours. The catalyst was removed by filtration and the filtrate was concentrated. Purification on silica gel (toluene/ethyl acetate) gave pure 69 in 22% yield. (Rf=0.43 toluene/ethyl acetate (7:3)); ESI-MS: M+H=159.2, M−H=161.8.

Example 18

Compounds are tested for their estrogen receptor activity in a binding assay and in a transactivation assay.

Determination of competitive binding to cytoplasmic human estrogen receptor α or β from recombinant CHO cells is used to estimate the relative affinity (potency ratio) of a test compound for estrogen receptors present in the cytosol of recombinant Chinese hamster ovary (CHO) cells, stably transfected with the human estrogen receptor α (hERα) or β receptor (hERβ), as compared with estradiol ($E_2$).

The estrogenic and antiestrogenic activity of compounds is determined in an in vitro bioassay with recombinant Chinese hamster ovary (CHO) cells stably co-transfected with the human estrogen receptor α (hERα) or β receptor (hERβ), the rat oxytocin promoter (RO) and the luciferase reporter gene (LUC). The estrogenic activity (potency ratio) of a test compound to stimulate the transactivation of the enzyme luciferase mediated via the estrogen receptors hERα or hERβ is compared with the standard estrogen estradiol. The antiestrogenic activity (potency ratio) of a test compound to inhibit the transactivation of the enzyme luciferase mediated via the estrogen receptors hERα or hERβ by the estrogen estradiol is compared with the standard ICI 164.384 (=(7α,17β)-N-butyl-3,17-dihydroxy-N-methylestra-1,3,5(10)-triene-7-undecanamide).

TABLE 1

| Compound | ERβ Transactivation | β/α ratio Transactivation | ERβ Binding |
|---|---|---|---|
| 67a | +++ | +++ | +++ |
| 67b | +++ | +++ | +++ |
| 67c | +++ | +++ | +++ |
| 67d | + | ++ | ++ |
| 67e | ++ | ++ | +++ |
| 69 | + | + | ++ |
| 25 | + | − | ++ |
| 68a | ++ | +++ | Nd |
| 68b | +++ | +++ | Nd |
| 2a | ++ | + | ++ |
| 2b | + | ++ | ++ |
| 2c | ++ | ++ | Nd |
| 2d | + | ++ | Nd |
| 5 | − | Nd | ++ |
| 60 | +++ | +++ | +++ |

Potency Transactivation (ERβ):
(% relative to 17β-estradiol)
− <0.1%
+ between 0.1–4%
++ between 4–10%
+++ >10%
β/α ratio Transactivation:
− <3.5
+ between 3.5–10
++ between 10–30
+++ >30
nd = not determined
Potency Binding (ERβ):
(% relative to 17β-estradiol)
− <0.1%
+ between 0.1–2%
++ between 2–10%
+++ >10%
nd = not determined

TABLE 2

Binding affinity of halogenated non-steroidal estrogens with ERα and ERβ

| Compound | Binding ERα | Binding ERβ |
|---|---|---|
| 7a | − | +++ |
| 7b | − | ++ |
| 7c | + | ++ |
| 7d | +++ | +++ |
| 8 | ++ | ++ |
| 10 | ++++ | ++++ |
| 60 | ++ | ++++ |

Binding: (% relative to 17β-estradiol)
− <0.3%
+ between 0.1–1.5%
++ between 1.5–3.5%
+++ between 3.5–8%
++++ >8%

What is claimed is:

1. A method of inducing an estrogenic or anti-estrogenic effect in a subject in need thereof, comprising:
administering an effective amount of a compound according to Formula I

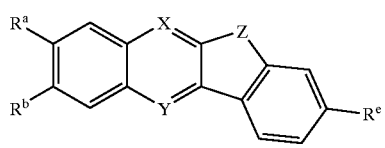

Formula I wherein,
one of $R^a$ or $R^b$ is '$R^e$ and the other is H;
$R^e$ and '$R^e$ are OH, optionally independently etherified or esterified;
X is N or —C($R^1$)—, wherein $R^1$ is H, halogen, CN, optionally substituted aryl, (1C–4C)alkyl, (2C–4C) alkenyl, (2C–4C)alkynyl or (3C–6C)cycloalkyl, which alkyl, alkenyl, alkynyl and cycloalkyl groups can optionally be substituted with one or more halogens;
Y is N or —C ($R^2$)—, with the proviso that X and Y are not both N, wherein $R^2$ has the same meaning as defined for $R^1$; Z is —C($R^3$, '$R^3$)— or —C($R^4$, '$R^4$)—C($R^5$, '$R^5$)—, wherein $R^3$, '$R^3$, $R^4$, '$R^4$, $R^5$, and '$R^5$, independently are H, (1C–4C)alkyl, (2C–4C)alkenyl or (3C–6C) cycloalkyl, which alkyl, alkenyl and cycloalkyl groups can optionally be substituted with one or more halogens.

2. A compound having formula II:

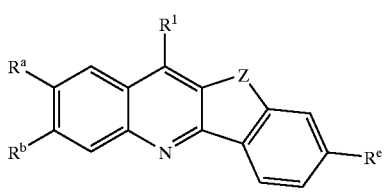

Formula II wherein,
one of $R^a$ or $R^b$ is '$R^e$ and the other is H;
$R^e$ and '$R^e$ are OH, optionally independently etherified or esterified;
$R^1$ is, halogen, CN, optionally substituted aryl, (1C–4C) alkyl, (2C–4C)alkenyl, (2C–4C)alkynyl or (3C–6C) cycloalkyl, which alkyl, alkenyl, alkynyl and cycloalkyl groups can optionally be substituted with one or more halogens;
Z is —C($R^3$,'$R^3$)— or —C($R^4$,'$R^4$)—C($R^5$, '$R^5$)—, wherein $R^3$, '$R^3$, $R^4$, '$R^4$, $R^5$, and '$R^5$, independently are H, (1C–4C)alkyl, (2C–4C)alkenyl or (3C–6C) cycloalkyl, which alkyl, alkenyl and cycloalkyl groups can optionally be substituted with one or more halogens.

3. The compound according to claim 2, wherein $R^a$ is '$R^e$ $R^b$ is H.

4. A compound having Formula V:

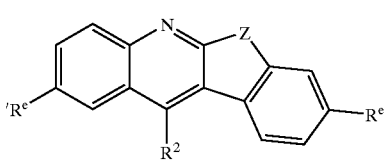

Formula V wherein,
$R^e$ and '$R^e$ are OH, optionally independently etherified or esterified;

Z is —C(R³,'R³)— or —C(R⁴,'R⁴)—C(R⁵,'R⁵)—,
wherein R³, 'R³, R⁴, 'R⁴, R⁵, and 'R⁵, independently are H, (1C–4C)alkyl, (2C–4C)alkenyl or (3C–6C)cycloalkyl, which alkyl, alkenyl and cycloalkyl groups can optionally be substituted with one or more halogens;

R² is H, halogen, CN, optionally substituted aryl, (1C–4C)alkyl, (2C–4C)alkenyl, (2C–4C)alkynyl, (3C–6C)cycloalkyl, which alkyl, alkenyl, alkynyl and cycloalkyl groups can optionally be substituted with one or more halogens.

5. The compound according to claim 4, wherein R³, 'R³, R⁴, 'R⁴, R⁵, and 'R⁵, independently are H or methyl.

6. A compound having Formula VI:

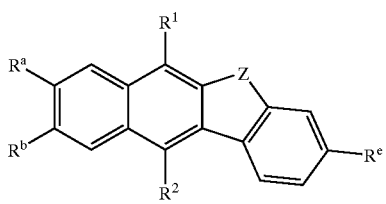

Formula VI wherein, one of $R^a$ or $R^b$ is $'R^e$ and the other is H;

$R^e$ and $'R^e$ are OH, optionally independently etherified or esterified;

R¹ and R² independently are H, halogen, CN, optionally substituted aryl, (1C–4C)alkyl, (2C–4C)alkenyl, (2C–4C)alkynyl or (3C–6C)cycloalkyl, which alkyl, alkenyl, alkynyl and cycloalkyl groups can optionally be substituted with one or more halogens;

Z is —C(R³,'R³)— or —C(R⁴,'R⁴)—C(R⁵,'R⁵)—, wherein R³, 'R³, R⁴, 'R⁴, R⁵, and 'R⁵, independently are H, (1C–4C)alkyl, (2C–4C)alkenyl or (3C–6C)cycloalkyl, which alkyl, alkenyl and cycloalkyl groups can optionally be substituted with one or more halogens.

7. The compound according to claim 6, having Formula VII:

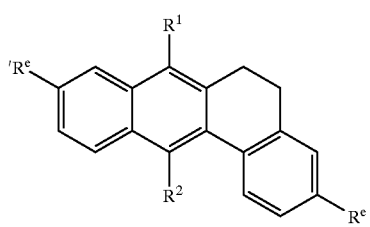

Formula VII wherein, $R^e$ and $'R^e$ are OH, optionally independently etherified or esterified;

R¹ and R² independently are H, halogen, CN, optionally substituted aryl, (1C–4C)alkyl, (2C–4C)alkenyl, (2C–4C)alkynyl or (3C–6C)cycloalkyl, which alkyl, alkenyl, alkynyl and cycloalkyl groups can optionally be substituted with one or more halogens.

8. The compound according to claim 6, having Formula VIII:

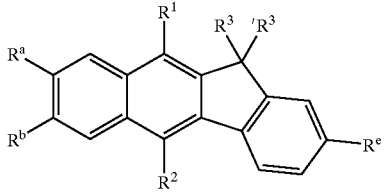

Formula VIII wherein, one of $R^a$ or $R^b$ is $'R^e$ and the other is H;

R¹ and R² independently are H, halogen, CN, optionally substituted aryl, (1C–4C)alkyl, (2C–4C)alkenyl, (2C–4C)alkynyl or (3C–6C)cycloalkyl, which alkyl, alkenyl, alkynyl and cycloalkyl groups can optionally be substituted with one or more halogens;

R³ and 'R³ independently are H or CH₃.

9. The compound according to claim 8, wherein $R^a$ is $'R^e$, $R^b$ is H, R³, 'R³ are H or methyl, R¹ or R² is H and the other of R¹ or R² is halogen, CN, optionally substituted aryl, (1C–4C)alkyl, (2C–4C)alkenyl, (2C–4C)alkynyl or (3C–6C)cycloalkyl, which alkyl, alkenyl, alkynyl and cycloalkyl groups can optionally be substituted with one or more halogens.

10. The compound according to claim 2, wherein R¹ is halogen or fluorine substituted methyl.

11. A pharmaceutical composition, comprising:
a compound according to claim 2, and
a pharmaceutically acceptable carrier.

12. The compound according to claim 4, wherein R¹ is halogen or fluorine substituted methyl.

13. The compound according to claim 6, wherein R¹ is halogen or fluorine substituted methyl.

14. A pharmaceutical composition, comprising:
the compound according to claim 4, and
a pharmaceutically acceptable carrier.

15. A pharmaceutical composition, comprising:
the compound according to claim 6, and
a pharmaceutically acceptable carrier.

16. A method of treating a patient requiring estrogen receptor therapy, comprising:
administering to the patient an effective amount of the compound according to claim 2.

17. The method according to claim 16, wherein the estrogen receptor therapy is effective for menopausal complaints, osteoporosis or estrogen dependent tumor control.

18. A method of contraception, comprising:
administering an effective amount of the compound according to claim 2 to prevent pregnancy.

19. A method of affecting estrogen receptor activity, comprising:
in vivo administration of a compound according to claim 2 to a patient.

20. A method of modulating a process mediated by an estrogen receptor, comprising:
administering to a patient an effective amount of a compound according to claim 2.

* * * * *